(12) United States Patent
Stoianovici et al.

(10) Patent No.: US 9,610,131 B2
(45) Date of Patent: Apr. 4, 2017

(54) ROTATING NEEDLE DRIVER AND APPARATUSES AND METHODS RELATED THERETO

(75) Inventors: Dan Stoianovici, Reistertown, MD (US); Doru Petrisor, Lutherville, MD (US); Dumitru Mazilu, Lutherville, MD (US); Alexandru Patriciu, Ancaster (CA); Lucian Gheorghe Gruionu, Dolj (RO)

(73) Assignee: The Johns Hopkins University, Baltimore, MD (US)

( * ) Notice: Subject to any disclaimer, the term of this patent is extended or adjusted under 35 U.S.C. 154(b) by 665 days.

(21) Appl. No.: 12/613,180

(22) Filed: Nov. 5, 2009

(65) Prior Publication Data
US 2010/0234856 A1 Sep. 16, 2010

Related U.S. Application Data

(60) Provisional application No. 61/111,543, filed on Nov. 5, 2008.

(51) Int. Cl.
| | |
|---|---|
| *A61F 11/00* | (2006.01) |
| *A61B 34/00* | (2016.01) |
| *A61B 34/30* | (2016.01) |
| *A61B 90/11* | (2016.01) |
| *A61B 10/02* | (2006.01) |

(52) U.S. Cl.
CPC .............. *A61B 34/70* (2016.02); *A61B 34/30* (2016.02); *A61B 90/11* (2016.02); *A61B 10/0233* (2013.01)

(58) Field of Classification Search
CPC ..... A61B 19/22; A61B 10/0233; A61B 90/11; A61B 34/70; A61B 34/10; A61B 34/20; A61B 2034/742; A61B 2034/2072; A61B 2017/3409
USPC ....................................................... 606/130, 1
See application file for complete search history.

(56) References Cited

U.S. PATENT DOCUMENTS

| | | | | |
|---|---|---|---|---|
| 3,450,081 | A | * | 6/1969 | Rabinow ........................ 112/221 |
| 3,993,523 | A | * | 11/1976 | Hunt et al. .................... 156/148 |
| 4,373,458 | A | * | 2/1983 | Dorosz et al. ........... 112/470.06 |
| 5,007,335 | A | * | 4/1991 | Orman et al. .................. 99/487 |
| 5,078,140 | A | * | 1/1992 | Kwoh .................... A61B 19/22 378/20 |
| 5,313,897 | A | * | 5/1994 | Katamine et al. ........ 112/470.13 |
| 5,391,156 | A | * | 2/1995 | Hildwein ............... A61B 17/29 411/503 |
| 5,441,505 | A | * | 8/1995 | Nakamura .................... 606/130 |
| 5,657,429 | A | * | 8/1997 | Wang .................... A61B 34/70 600/118 |

(Continued)

*Primary Examiner* — Richard Louis
(74) *Attorney, Agent, or Firm* — Mintz Levin Cohn Ferris Glovsky and Popeo, P.C.; Peter F. Corless; Richard B. Emmons

(57) ABSTRACT

Featured is a medical instrument driver, a robotic apparatus embodying such a medical instrument driver and methods related thereto for inserting a medical instrument into tissue of a mammal (e.g., human). Such medical instruments include medical needles, biopsy needles, trocars, cutters and introducers. Such a medical instrument driver according to the present invention is configured and arranged so that medical instrument is rotated as it is being moved longitudinally for insertion into the tissue such that the medical instrument is spiraling as it pierces and traverses the tissue to the target area.

18 Claims, 17 Drawing Sheets

(56) References Cited

U.S. PATENT DOCUMENTS

| | | | |
|---|---|---|---|
| 5,695,500 A * | 12/1997 | Taylor | A61B 34/20 606/130 |
| 5,697,939 A * | 12/1997 | Kubota | A61B 19/201 606/130 |
| 5,957,933 A * | 9/1999 | Yanof et al. | 606/130 |
| 6,285,902 B1 * | 9/2001 | Kienzle et al. | 600/427 |
| 6,400,979 B1 | 6/2002 | Stoianovici et al. | |
| 6,451,027 B1 * | 9/2002 | Cooper | A61B 1/00149 606/130 |
| 6,626,848 B2 | 9/2003 | Neuenfeldt | |
| 6,857,609 B2 | 2/2005 | Stoianovici et al. | |
| 7,021,173 B2 * | 4/2006 | Stoianovici et al. | 74/490.05 |
| 7,086,309 B2 | 8/2006 | Stoianovici et al. | |
| 7,247,116 B2 | 7/2007 | Stoianovici et al. | |
| 7,297,142 B2 | 11/2007 | Brock | |
| 2002/0111634 A1 * | 8/2002 | Stoianovici et al. | 606/129 |
| 2005/0178307 A1 * | 8/2005 | Frazer et al. | 112/117 |
| 2006/0161136 A1 * | 7/2006 | Anderson et al. | 606/1 |
| 2007/0034046 A1 | 2/2007 | Stoianovici et al. | |
| 2007/0137371 A1 * | 6/2007 | Devengenzo et al. | 74/490.01 |
| 2007/0156157 A1 * | 7/2007 | Nahum et al. | 606/130 |
| 2008/0249651 A1 * | 10/2008 | Hosek | B25J 9/042 700/121 |
| 2009/0192521 A1 * | 7/2009 | Braun | A61B 17/29 606/130 |

\* cited by examiner

ROTATING NEEDLE DRIVER AND APPARATUSES AND METHODS RELATED THERETO

This application claims the benefit of U.S. Provisional Application Ser. No. 61/111,543 filed Nov. 5, 2008, the teachings of which are incorporated herein by reference.

STATEMENT REGARDING FEDERALLY-SPONSORED RESEARCH

The present invention was supported by a grant from the National Institute of Health, grant number CA094274. The U.S. Government may have certain rights to the present invention.

FIELD OF INVENTION

The present invention generally relates to apparatuses, devices and methods for the insertion of medical needles and other medical instruments into tissue and more specifically to apparatuses, devices and methods for the insertion of medical instruments such as medical needles, biopsy needles, trocars, cutters and introducers into tissue while rotating the medical instrument as it is being moved longitudinally for insertion into the tissue.

BACKGROUND OF THE INVENTION

Image-guided robots are manipulators that operate based on medical images. These are modern medical tools with applications in most medical fields, allowing the physicians to perform interventions not only under direct vision, but with the additional help of the transcutaneous data. Significant research efforts around the world are dedicated to the development of these systems, and a few are already in commercial stages.

Perhaps the most common class of image-guided robots are the robots for needle interventions; robots that help manipulate needles in procedures such as biopsies, therapeutic injections, thermal ablations, brachytherapy, as part of surgical procedures such as percutaneous kidney stone extraction, etc. Needle robots have been investigated in conjunction with all types of imaging equipment (e.g., x-ray, CT, and most recently with the MRI, such as MrBot [see U.S. Pat. Nos. 7,086,309 and 7,247,116; US. Publication No. 2007/0034046 the teachings of which are incorporated herein by reference and see also Stoianovici D, Song D, Petrisor D, Ursu D, Mazilu D, Muntener M, Schar M, Patriciu A: "MRI Stealth" Robot for Prostate Interventions. *Minimally Invasive Therapy & Allied Technologies.* 2007; Vol. 16(4) pp. 241-248]. These have the potential to precisely target the disease or the intervention site in a percutaneous, minimally invasive, less traumatic, least disruptive fashion. Unlike humans, robots and imagers are digital devices, allowing for a direct communication and manipulation of the instruments in the image space, while being coordinated and supervised by the physician.

If a point is identified in the images, for example, some of these robots (e.g., RCM—U.S. Pat. No. 7,021,173, the teachings of which are incorporated herein by reference; and AcuBot [see Stoianovici D, Cleary K, Patriciu A, Mazilu D, Stanimir A, Craciunoiu N, Watson V, Kavoussi L R: AcuBot: A Robot for Radiological Interventions. *IEEE Transactions on Robotics and Automation.* October 2003; Vol. 19(5) pp. 926-930] can orient the needle so that it points at the corresponding location in the patient. Most needle robots position and/or orient a needle guide and the needle insertion is than performed manually by the physician by inserting the needle through the guide. A few systems include automated means of inserting the needle using needle drivers (e.g., U.S. Pat. No. 6,400,979, the teachings of which are incorporated herein by reference).

There are simplicity advantages in manually inserting the needle through a guide. These include, for example, keeping the physician in direct control of the needle, and perhaps allowing for simpler regulatory approvals in using these image-guided systems in clinical trails and practice. However, manual insertion of the needle is a compromise which reduces the utility of a fully automated system. Depending on the application this may be controversial, but they are numerous situations when needle drivers would be preferable. For example, when x-ray based imagers are used, manual insertion would require the hands of the physician to be in the field of the x-rays. Thus, the physician can quickly accumulate exposure with the numerous procedures done on a daily basis.

Also, to reach inside CT scanners, the physician would need to stretch over the patient, and this could inadvertently change the trajectory of the needle while it is being inserted. In addition, inside closed bore MRI scanners it is not feasible to reach in by hand because these MRI scanners are typically narrow long tunnels. In any case, a manual needle insertion can lead to the possibility of insertion depth errors.

Further, needle insertion is a translation movement and translation stages typically are physically larger than their stroke. Also, linear motion is typically implemented using a translational joint. Additionally, there are a few needle drivers available commonly that hold the needle by its head. This is disadvantageous because it maximizes the unsupported length of the needle, reducing its lateral stiffness.

There is found in U.S. Pat. No. 7,297,142, a system and associated method for delivering a selected one of a plurality of instruments to an internal body site. An instrument storage chamber is providing having passages for separately accommodating a plurality of instruments. An outlet guide tube couples from the instrument storage chamber and receives a selected one of these instruments for delivery to an internal operative site. An indexing mechanism is provided associated with the chamber for causing relative displacement between the instruments and the outlet guide tube. An instrument driver displaces the registered instrument from the chamber into the outlet guide tube for delivery to the internal operative site.

There is found in U.S. Pat. No. 6,626,848, devices and methods to reduce the insertion force of a medical needle using reciprocal rotation motion about the longitudinal axis. The device converts continuous rotational motion to reciprocal rotational motion for the beveled needle. A needle using reciprocal rotational motion creates a slit in the tissue, sufficient in size to equal the maximum circumference of the needle prior to insertion of the needle. The insertion force will decrease as the speed of the reciprocal rotational motion increases until a steady state insertion force is achieved.

It thus would be desirable to provide a new device and methods for driving a medical instrument such as a needle into tissue(s). It would be particularly desirable to provide such a device and method that would utilize rotational movement in conjunction with translation movement of the needle to facilitate entry of the driven medical instrument into the tissue(s) to the desired location. It also would be desirable to provide such a device and methods including a translational driving mechanism that can be used in confined spaces such as when using MRI scanners and CT scanners as compared to prior art needle driving devices and related methods. Such needle driving devices and methods preferably would be simple in construction and less costly than prior art devices and such methods would not require users more skilled than those using conventional devices and methods.

SUMMARY OF THE INVENTION

The present invention features a medical instrument driver, an apparatus embodying a robotic device and such a medical instrument driver and methods related thereto for inserting a medical instrument into tissue of a mammal more specifically the tissue of a human. Such medical instruments include medical needles, biopsy needles, trocars, cutters and introducers. In its broadest aspects such a medical instrument driver is configured and arranged so that the medical instrument is rotated as it is being moved longitudinally for insertion into the tissue.

This combined rotating and translating of the medical instrument causes the medical instrument to spiraling as it pierces and traverses the tissue to the target area instead of deflecting on a side as with conventional drivers. In this way, the inserted end of the medical instrument ends up closer to the target as compared to conventional drivers.

Such spiraling motion also should break the static friction between the tissue and the target reducing forces, as well as possibly reducing insertion forces by the "drilling" effect of the spiral motion. It also is expected that such rotating and translating movement of the medical device collectively reduces deformations by reducing interaction forces, as strains are directly related to stress.

Commonly, the highest causes of errors in aiming an in-situ target with the point of the needle are deflections: soft tissue deflections and needle bending. These are related, so that thin needles cause less tissue deflections but bend more, whereas thicker needles don't bend as much but push the tissues. Apparently, there is no satisfactory compromise solely based on the gauge of the needle, and in fact most of the time needles are selected based on other clinical or availability criteria. Say that even before the insertion the needle is ideally oriented pointing at the target, when inserted the needle does not exactly aim at the target. Such errors are larger or smaller and also depend on other factors such as respiration-induced motion for example, but additional mechanisms are needed for improved targeting.

In further embodiments, the medical instrument driver of the present invention, provides other degrees of freedom (DOF) and auxiliary features to assist in performing its main and other functions. Such a medical instrument driver is configurable so it can be used independently, handheld or be supported by a positioning arm such as for example, the positioning arm and apparatus found in U.S. Pat. No. 6,857,609 (the teachings of which are incorporated herein by reference) or the end-effector (EEF) of a robot. This decouples the orientation and/or positioning of the needle done by the robot from the insertion undertaken by the medical instrument driver of the present invention.

In an illustrative exemplary embodiment, the medical instrument driver is attached to the Remote Center of Motion (RCM) robotic orientation module described in U.S. Pat. No. 7,021,173 (the teachings of which are incorporated herein by reference). In another illustrative exemplary embodiment, such a medical instrument driver replaces the PAKY needle driver as taught in U.S. Pat. No. 6,400,979 (the teachings of which are incorporated herein by reference) used with an AcuBot robot. In such cases, the medical instrument driver is supported by the RCM, passive positioning arm, a 3DOF Cartesian positioning stage, and/or a bridge support over the table.

In more particular embodiments, there is featured a medical instrument driver operable coupled to a medical instrument for causing the medical instrument to be inserted into tissue. Such a medical instrument driver includes a translation and rotational mechanism operably coupled to one portion of the medical instrument and a distal support that is distal from the translation and rotational mechanism, which includes a through aperture in which a distal portion of the medical instrument is slidably disposed. The distal support and the translation and rotational mechanism are arranged so the medical instrument distal portion moves through the distal support through aperture such that an insertable end of the medical instruments exits the through aperture and is inserted into the tissue. The medical instrument includes but is not limited to, a medical needle, a biopsy needle, a trocar, a cutter or an introducer.

Such a translation and rotational mechanism includes a pivoting structure and a rotational structure. The pivoting structure is configured so as to cause the medical instrument to move along a long axis of the medical instrument responsive to rotational movement of an end of the pivoting structure. The rotational structure is configured so as to cause the medical instrument to rotate about the long axis as the medical instrument moves along the long axis. In further embodiments, the translation and rotational structures cooperate so that the medical instrument in effect spirals into the tissue(s).

In yet further embodiments, the translation structure includes a plurality of rotary joints. In more particular embodiments, the translation structure includes a crank member disposed between a first rotary joint and second rotary joint; a rod member extending between the second rotary member and a fourth rotary joint. The fourth rotary joint is operably coupled to the medical instrument and the translation structure further includes a slider joint that is slidably coupled to the rod member and disposed between the second and fourth rotary joints.

In yet further embodiments, such a medical instrument driver further includes a motor that is operably coupled to the first rotary joint such that rotation of the motor drives the crank member to move and so such rotation of the motor also thereby causes an end point of the rod member to move essentially along a linear trajectory. Such a translation structure also further includes a plurality of pulleys disposed at each of the first, second and fourth rotary joints and first and second belt members. One belt member is arranged so as to extend between the pulleys at the first and second rotary joints and the second belt member is arranged so as to extend between the pulleys at the second and fourth rotary joints.

The translation and rotational mechanism of the present invention is particularly advantageous as it yields a compact design as compared to conventional drivers and so that the medical instrument driver of the present invention is less tall than the medical device, e.g., needle. This compactness is particular advantageous as it allows for fitting the driver of the present invention into the compact space of the imagers. As indicated above, needle insertion is a translation and conventional translation stages typically are larger than their stroke. The translational structure of the present invention on the other hand embodies an optimized crank hinged slider rod mechanism that renders near translational motion with a compact design. Also, linear motion with conventional drivers is implemented using a translational joint. In the present invention, such linear motion or near linear motion is accomplished using a combination of rotary joints.

In yet further embodiments, the rotational structure includes a drive motor and gears that are arranged so as to operably couple the medical instrument and the drive motor.

In yet further embodiments/aspects, such a medical instrument driver further includes a first adapter and a second adapter. The first adapter is configured so as to operable couple a given medical instrument to the translational and rotational mechanism and the second adapter is configured so as to operable couple the given medical instrument to the distal support.

Such adapters provide a mechanism by which standard medical instruments (e.g., standard needles) can be used with the medical instrument driver of the present invention, as such standard medical instruments can be mounted in adapters that can be customized for use with such a medical instrument and the driver of the present invention.

The first adapter is particularly configured so as to encase the head of the needle and its stylet and so as to also present a spur gear for engaging the needle in rotary motion. The needle nozzle or insertable medical instrument end is similarly held by the second adapter bottom and more particularly matches the diameter and/or cross section of the medical instrument being used.

In yet further embodiments/aspects, such a medical instrument driver of the present invention further includes a set of force sensors to measure the interaction force of the nozzle with the patient and the force of needle insertion. These can be used either to substitute for part of the interaction that the physician normally has in handling the needle, or to provide additional information that is not used in the manual case. For example, a master-slave manipulation system can be implements between a haptic interface and the a robot including the medical instrument driver, respectively. In such a case, the physician can feel the forces experienced by the robot handling the needle. Alternatively, the interaction of the needle nozzle (distal support) with the skin entry point can be used to sense patient motion, including respiratory motion. Moreover, additional real time information are extractable from the nozzle forces with respect to the direction and magnitude of needle bending.

When using conventional drivers, there typically is no information available to determine the direction of the needle during insertion as needle targeting errors depend on complex factors such as the type of soft tissues, needles used, experience of the physician, or the depth of the target, the errors of the imager, etc. Thus, it is unfortunately true that when a needle is advanced to a desired target using conventional drivers, its final destination is uncertain. Also, when the point of the needle disappears entering the body, no proper imagers are available to follow it in real time. This is because that "good" (i.e., geometrically consistent, high soft tissue image quality) imagers are not real time, and vice versa. As the distal support or nozzle thereof of the present invention holds the direction of the needle and measures the interaction of the needle with the tissues, this can be utilized to provide real-time information regarding the direction of needle deflection, which in turn can be used as a feedback for corrections by accordingly positioning and orienting the needle.

According to another aspect of the present, there is featured an apparatus for causing a medical instrument to be inserted into tissue, that includes a robotic device having an arm that is movable in one or more dimensions; and a medical instrument driver operable coupled to the medical instrument and operably coupled to the robotic arm, where the robotic arm is movable so as to position the medical instrument driver with respect to a target area. Such a medical instrument driver includes a translation and rotational mechanism operably coupled to one portion of the medical instrument and one portion of the robotic arm, a distal support that is operably coupled to another portion of the robotic arm and which is distal from the translation and rotational mechanism. Such a distal support includes a through aperture in which a distal portion of the medical instrument is slidably disposed. Also, the distal support and the translation and rotational mechanism are arranged so the medical instrument distal portion moves through the distal support through aperture such that an insertable end of the medical instrument exits from the aperture and is inserted into the tissue.

Such a translation and rotational mechanism includes a pivoting structure and a rotational structure. The pivoting structure is configured so as to cause the medical instrument to move along a long axis of the medical instrument responsive to rotational movement of an end of such structure. The rotational structure is configured so as to cause the medical instrument to rotate about the long axis as the medical instrument moves along the long axis. In more particular aspects/embodiments, the translation and rotational structures cooperate so that the medical instrument spirals into the tissue and the medical instrument is one of a medical needle, a biopsy needle, a trocar, a cutter or an introducer. Such an apparatus can further embody any of the above described features of a medical instrument driver according to the present invention.

Also features are methods for inserting a medical instrument into tissue of a mammal more specifically the tissue of a human. Such medical instruments include medical needles, biopsy needles, trocars, cutters and introducers. In its broadest aspects such methods of the present invention result in a medical instrument being rotated as it is being moved longitudinally for insertion into the tissue.

In more particular aspects/embodiments, such methods of the present invention include providing a medical instrument driver including a translation and rotational mechanism having a pivoting structure configured so as to cause a medical instrument to move along a long axis of the medical instrument, and a rotational structure configured so as to cause the medical instrument to rotate about the long axis as the medical instrument moves along the long axis; and a distal support which is distal from the translation and rotational mechanism, said distal support including a through aperture in which a distal portion of the medical instrument is slidably disposed; and operably coupling one portion of the medical instrument to the translation and rotational mechanism and slidably coupling another portion of the medical instrument to the distal support. Such a method also includes positioning the distal support, so an insertable end of the medical instrument is oriented towards a target area; and operating the translation and rotational mechanism so as to cause the medical instrument distal portion to move through the distal support through aperture such that the insertable end is inserted into the tissue.

The provided medical instrument driver provided in such methods, can further embody any of the features of a medical instrument driver according to the present invention as described herein.

Other aspects and embodiments of the invention are discussed below.

DEFINITIONS

The instant invention is most clearly understood with reference to the following definitions:

RCM shall be understood to mean Remote Center of Motion.

RCM module shall be understood to mean a RCM orientation module as is known to those skilled in the art.

EEF shall be understood to mean an end-effector of a robot.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1A:
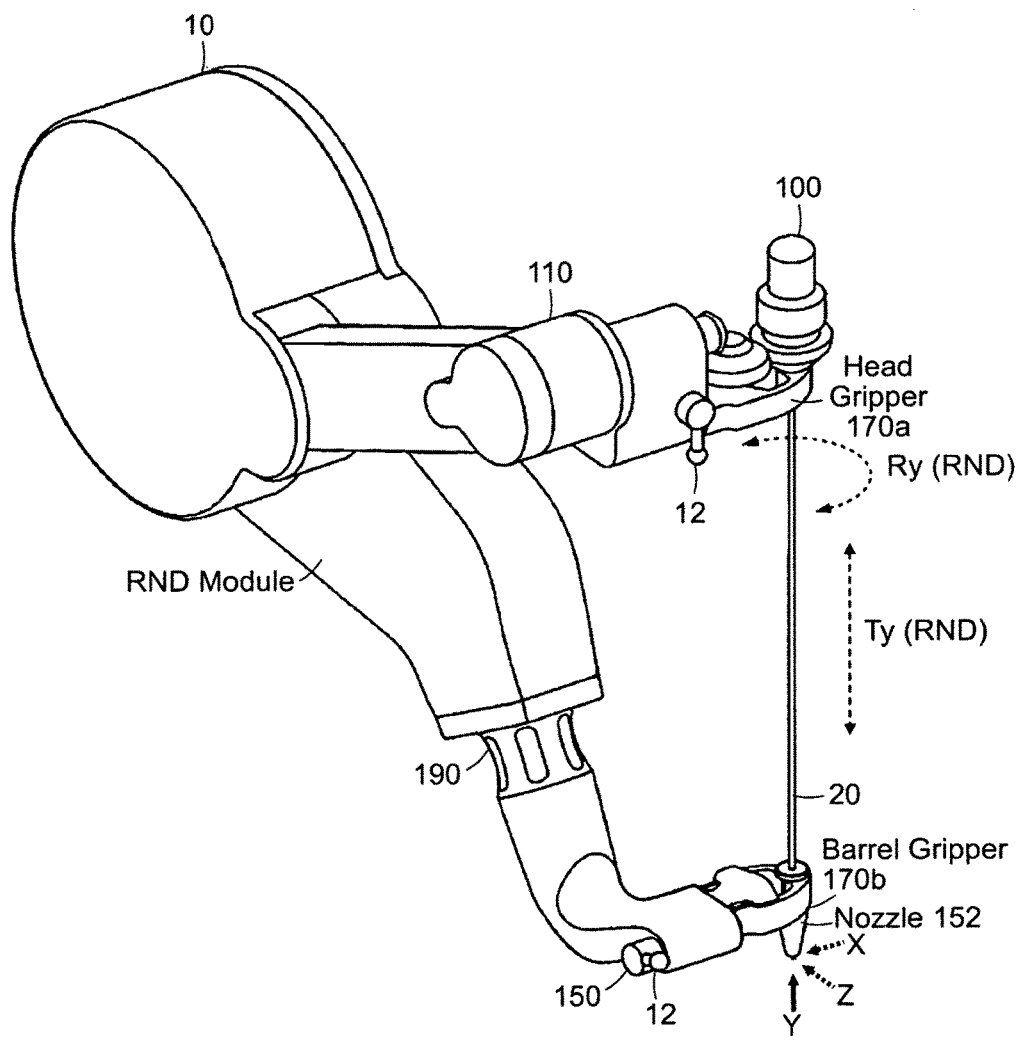
FIG. 1A is an axonometric view of a medical instrument driver according to the present invention mounted to an RCM orientation module.
Figure 1B:
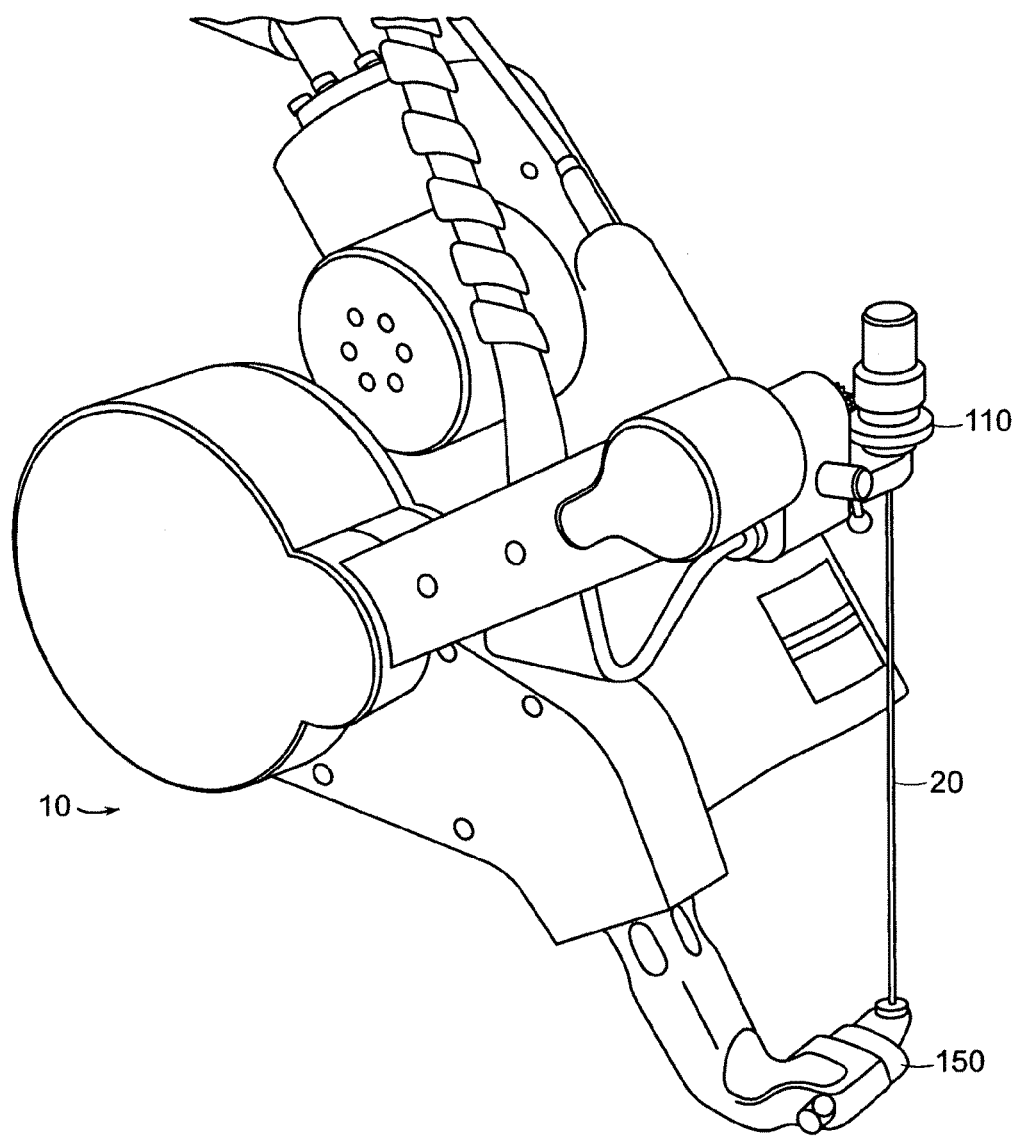
FIG. 1B is a pictorial view of the medical instrument driver mounted to the RCM module and further mounted to a positioning arm.
Figure 1C:
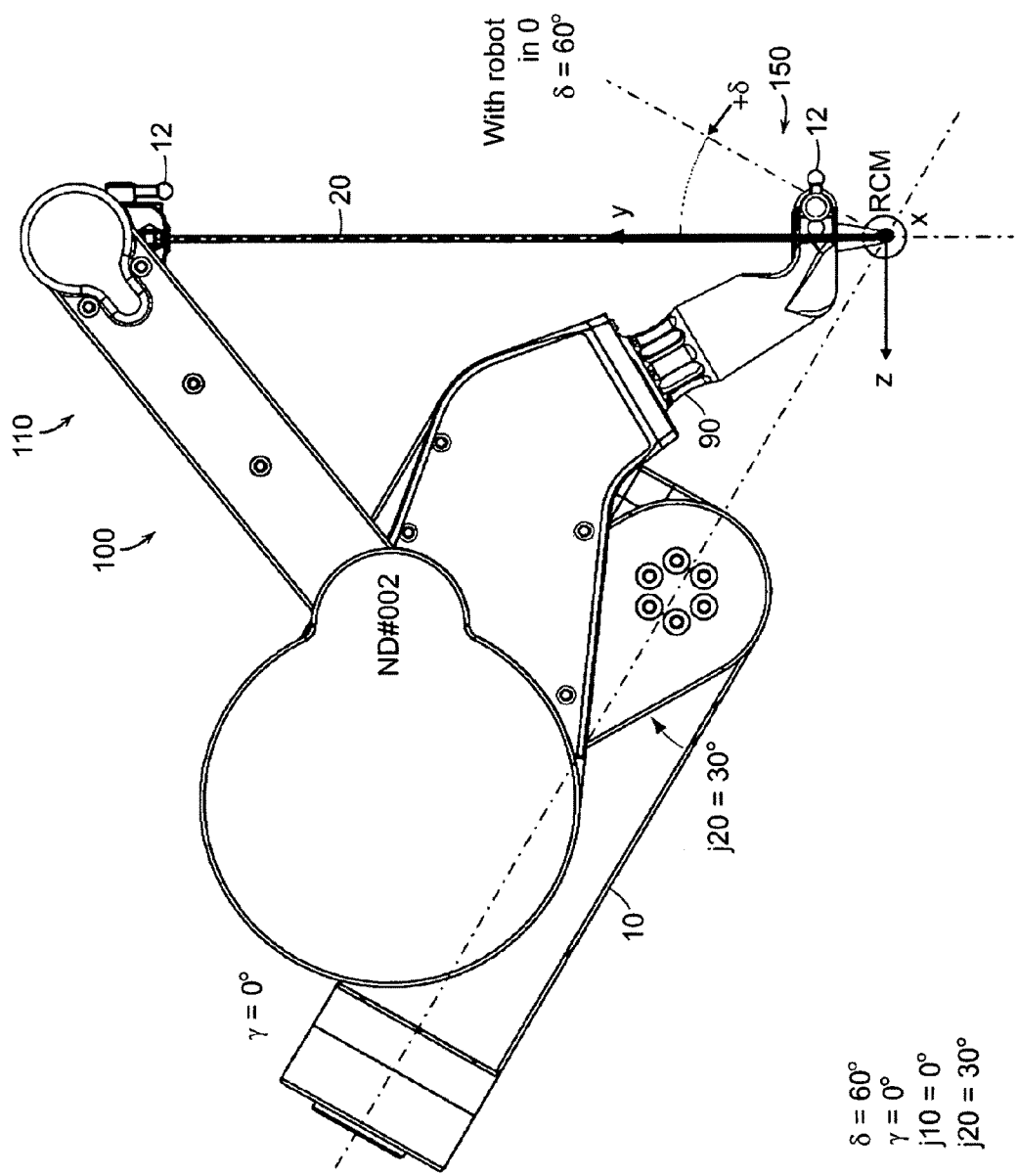
FIG. 1C is a side view of the medical instrument driver of FIG. 1A showing the setup with the RCM orientation module.
Figure 1D:
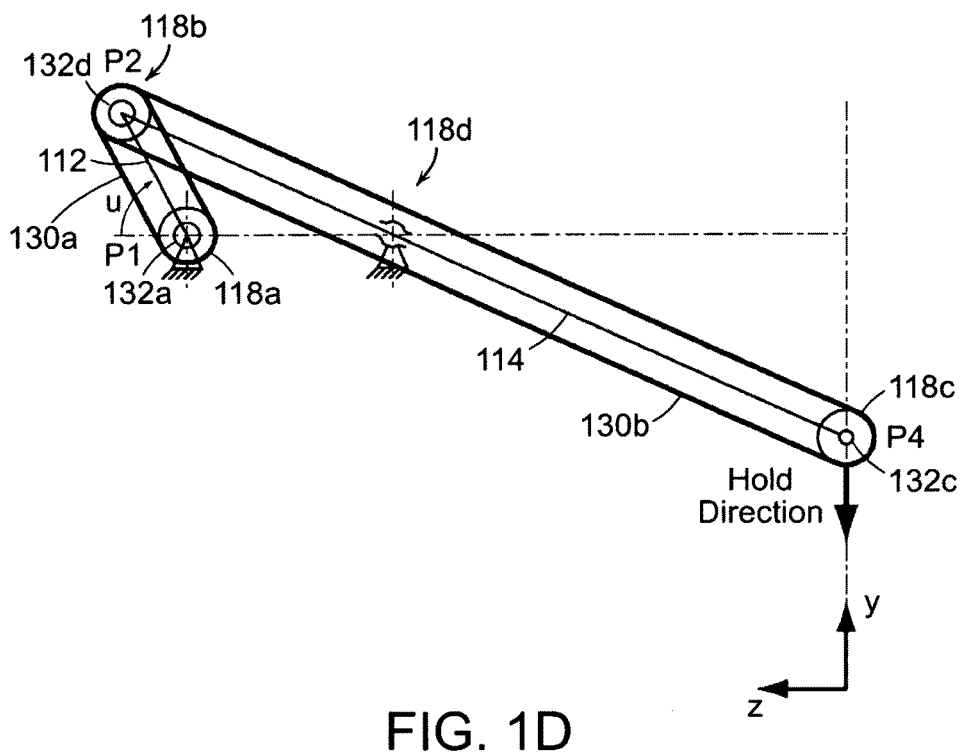
FIG. 1D is an exemplary view showing the parallel motion mechanism for controlling the direction of the needle, comprising the translational structure of the medical instrument driver of FIG. 1A.
Figure 1E:
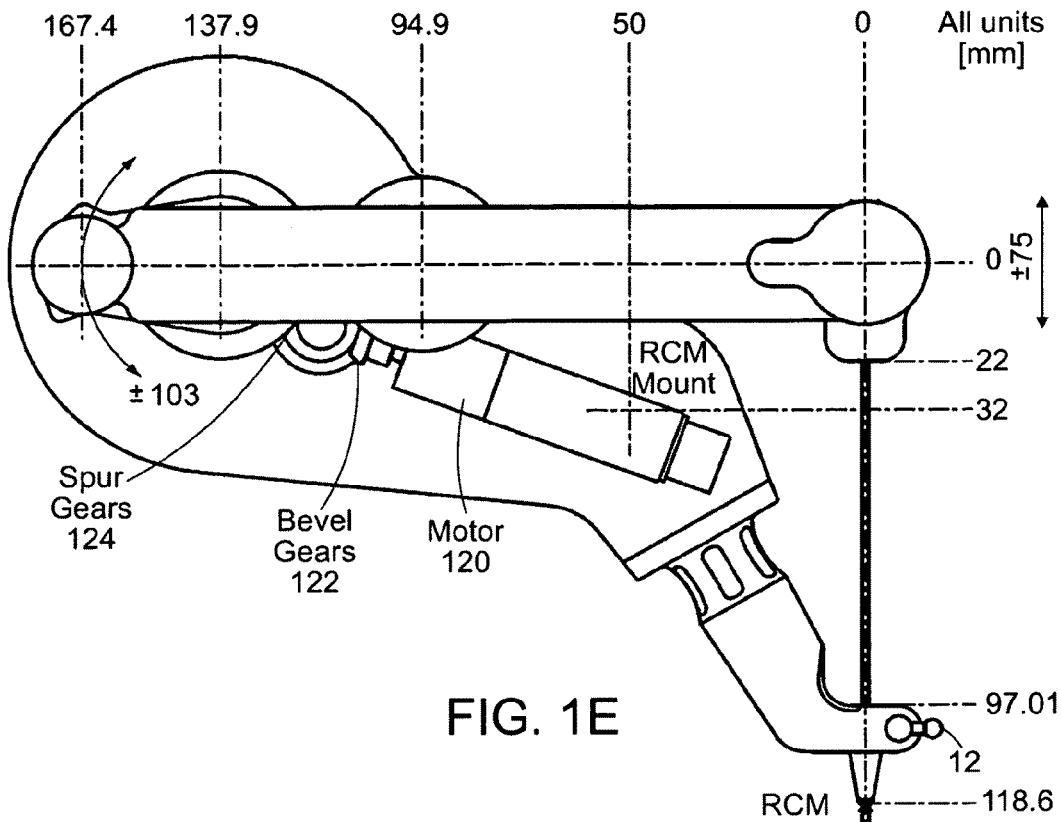
FIG. 1E is a side view of the medical instrument driver of FIG. 1A.
Figure 1F:
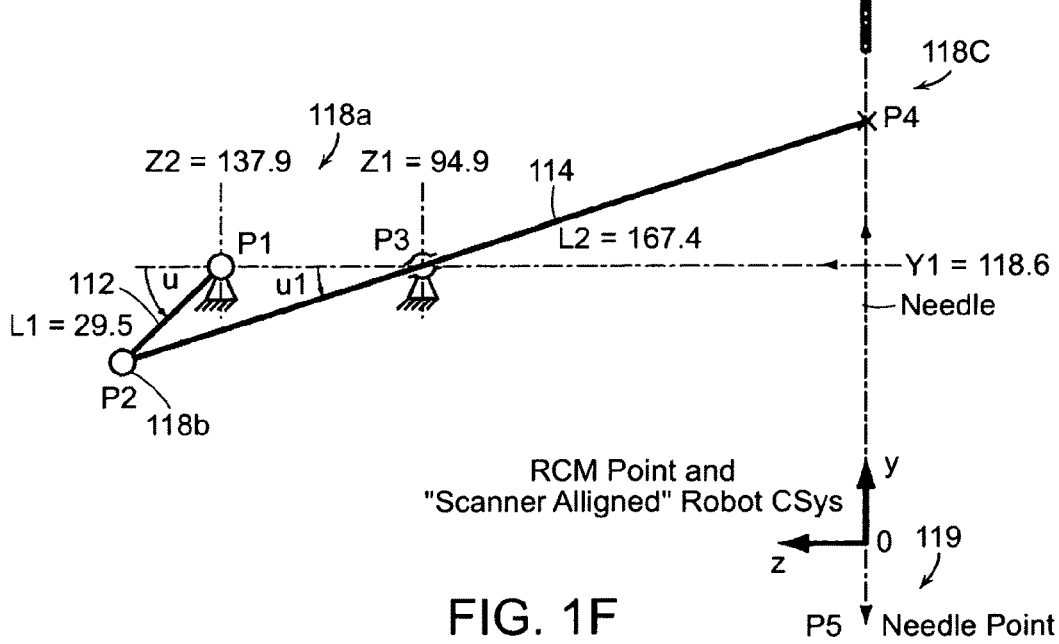
FIG. 1F is a schematic view of a medical instrument driver of the present invention.

Referring now to the various figures of the drawing wherein like reference characters refer to like parts, there is shown in FIGS. 1A-F various views illustrating a medical instrument device driver 100 of the present invention, functionalities thereof and other views describing design features thereof. More particularly, an axonometric view of a medical instrument driver according to the present invention mounted to an RCM orientation module is shown in FIG. 1A; a pictorial view of the medical instrument driver mounted to the RCM module and further mounted to a positioning arm is shown in FIG. 1B; a side view of the medical instrument driver of FIG. 1A showing the setup with the RCM orientation module is shown in FIG. 1C; an exemplary view showing the parallel motion mechanism for controlling the direction of the needle, comprising the translational structure of the medical instrument driver of FIG. 1A is shown in FIG. 1D; a side view of the medical instrument driver of FIG. 1A is shown in FIG. 1E; and a schematic view of a medical instrument driver of the present invention is shown in FIG. 1F.

Such a medical instrument driver (RND) 100 is mounted to a RCM orientation module 10 and includes an upper mechanism 110 that embodies the mechanisms to translate the medical instrument 20 for insertion into the tissue and also rotate the medical instrument as it is being translated to facilitate insertion of the medical instrument into the tissue. Such a medical instrument driver 100 also includes a lower mechanism 150 that is configured and arranged so that a distal portion of the medical instrument 20 is slidably disposed within the lower mechanism and to limit movement of the medical instrument in a plane that is perpendicular to the long axis of the needle.

It should be recognized that the medical instrument 20 includes any of a number of instrumentalities as are known to those skilled in the art, which are insertable into tissue(s) using a translation motion or a combination of translation and rotary motion. Such medical instruments include, but are not limited to medical needles, biopsy needles, trocars, cutters and introducers. For simplicity, the following discussion refers to medical needles or needles 20, however, this shall not be construed as limiting the scope of the invention to needles.

As is known to those skilled in the art, the RCM orientation module is a 2 degrees of freedom (DOF) robotic orientation module which is capable of orienting an EEF in two orthogonal directions (Rx and Rz) while maintaining a fixed location of a point (RCM Point). For the medical instrument driver 100, this fulcrum point is located at the tip of a nozzle 152 embodied in the lower mechanism 150. It also should be recognized that the configuration and arrangement of the medical instrument driver 100 of the present invention also present two decoupled DOF for inserting the needle (Ty) and spinning it (Ry).

In operation the nozzle 152 is placed at the desired skin entry point, so that before inserting the needle 20, the orientation of the needle can be adjusted with the RCM by pivoting about the skin entry point. The nozzle 152 is placed on the skin, the orientation is adjusted (with the RCM) so that the needle 20 points towards the desired target, and then the needle 20 is advanced using the medical instrument driver 100. Decoupling these motions according to the phases of the intervention provides a medical safety feature because the inactive module can be locked in the inactive phase. For example, the medical instrument driver is essentially locked during the needle orientation phase thereby providing assurances that the needle is not inadvertently advanced before the proper orientation is confirmed.

Although described herein in connection with a RCM orientation module 10, this shall not be construed as limiting apparatuses, systems and the medical instrument driver 100 of the present invention. Such a medical instrument driver is configurable so it can be used independently, handheld or be supported by a positioning arm such as for example, the positioning arm and apparatus found in U.S. Pat. No. 6,857,609 (the teachings of which are incorporated herein by reference) or the end-effector (EEF) of a robot. This decouples the orientation and/or positioning of the needle done by the robot from the insertion undertaken by the medical instrument driver of the present invention. In further embodiments, the medical instrument driver of the present invention, provides other degrees of freedom (DOF) and auxiliary features to assist in performing its main and other functions.

In an illustrative exemplary embodiment, the medical instrument driver 100 is attached or coupled to the Remote Center of Motion (RCM) robotic orientation module described in U.S. Pat. No. 7,021,173 (the teachings of which are incorporated herein by reference). In another illustrative exemplary embodiment, such a medical instrument driver 100 replaces the PAKY needle driver as taught in U.S. Pat. No. 6,400,979 (the teachings of which are incorporated herein by reference) used with an AcuBot robot. In such cases, the medical instrument driver is supported by the RCM, passive positioning arm, a 3DOF Cartesian positioning stage, and/or a bridge support over the table.

As indicated above, the upper mechanism 110 of the medical instrument driver 100 embodies the mechanisms for translating and rotating the needle for purposes of inserting the needle into tissues of a mammal, more particularly a human. Reference to patient or tissues of patient in the following shall be understood to mean tissue of a mammal or human and that the patient is a mammal or human. This combined translating and rotational movement of the needle 20 results in the needle being advanced in a drill like or spiral motion. This has several advantages.

Commonly, the highest causes of errors in aiming an in-situ target with the point of the needle are deflections: soft tissue deflections and needle bending. For example, the needle deflects on a side, and it ends out further from the target. These are related, as thin needles cause less tissue deflections but bend more, whereas thicker needles do not bend as much but push the tissues. There is apparently, no satisfactory compromise solely based on the gauge of the needle, and in fact most of the time needles are selected based on other clinical or availability criteria. Say that before the insertion the needle is ideally oriented pointing at the target. Even so, when inserted the needle does not exactly aim at the target. The errors are larger or smaller and also depend on other factors such as respiration-induced motion for example, but additional mechanisms are needed for improved targeting.

The spinning translating needle resulting from the translating, rotating movement resulting from operation of the medical instrument driver 100 of the present invention, causes the needle 20 to spiral in, rather than deflecting on a side, and so the needle ends out closer to the target. Such spinning translating needle movement also should break the static friction between the tissue and the target thereby reducing forces and further possibly reducing insertion forces. Such spinning translating needle movement also collectively, reduces deformations by reducing interaction forces, as strains are directly related to stress.

As described hereinafter, the configuration and arrangement of the medical instrument driver 100 as well as the kinematics and design embodied in such a driver, allows for a compact design, so that the driver is less tall than the needle. This is particularly advantageous for locating such a medical instrument driver in the compact space of imagers. In contrast, typical translation stages for needle insertion are larger than their stroke. Also, the crank hinged slider rod mechanism described hereinafter, that is embodied in the medical instrument driver 100, renders near translational motion with a compact design.

The are a few needle drivers that are commonly available that hold the needle by its head. This is disadvantageous because it maximizes the unsupported length of the needle reducing its lateral stiffness. While the medical instrument driver 100 also can support the needle from its head, such a driver provides an additional needle support guide, the lower mechanism 150, which is located, in use, in close proximity of the skin entry point. This is similar to holding a needle with two hands, one from its head and one from its barrel next to the skin, where one hand pushes the needle in and out, and the lower holds the guide to support the direction of the needle as close as possible to the skin. In the present invention, the upper mechanism 110 provides support and structure for moving the needle 20 and the lower mechanism 150 provides the guiding support for the needle. In further embodiments, the lower mechanism 150, more particularly the needle nozzle 152, also encases the sharp needle point before insertion to protect the patient and medical personnel.

As described hereinafter such upper and lower mechanisms 110, 150 are respectively configured so as to include release mechanisms or grippers 170*a,b* that releasably retain the needle and adapters 180*a,b* thereof in such upper and lower mechanisms. Such release mechanisms or grippers 170*a,b* are generally configured so as to release the needle 20 quickly, automatically, and very smoothly, without moving or pushing on the needle. This is convenient for handling multiple needles, releasing an inserted needle, and also as a safety feature.

As described in further detail below, the medical instrument driver 100 of the present invention utilizes adapters 180*a,b* or customized adapters so such a medical instrument driver can be used with standard medical instruments or medical needles. One of these adapters 180*a*, a needle head adapter, is configured to encase the head of the needle 20 so it is locked to its stylet and also presents a mechanism (e.g., spur gear) so as to allow the needle to be rotated about its long axis.

The barrel adapter 180*b* which includes the needle nozzle 152, is embodied in the lower mechanism 150 and is matched to the diameter of the needle being used. As these two needle adapters 180*a,b* come in direct contact with the needle 20, they are made from any of a number of materials known to those skilled in the art that are appropriate for the intended use. In exemplary embodiments, the adapters are made from any of a number of medical grade plastics.

As also described in further detail below, the medical instrument driver 100 of the present invention includes one or more sets of sensors 190*a,b* to measure (a) the interaction force of the nozzle 152 with the patient and (b) the force of needle insertion. These sensors 190*a,b* can be used either to substitute for part of the interaction that the physician normally has in handling the needle, or to provide additional information that is not used in the manual case. For example, a master-slave manipulation system can be created between a haptic interface and the RND robot respectively. With this, the physician can feel the forces experienced by the robot handling the needle. Alternatively, the interaction of the needle nozzle 152 with the skin entry point can be used to sense patient motion, including respiratory motion. Moreover, additional real time information can be extracted from the nozzle forces with respect to the direction and magnitude of needle bending.

When using conventional drivers, there typically is no information available to determine the direction of the needle during insertion as needle targeting errors depend on complex factors such as the type of soft tissues, needles used, experience of the physician, or the depth of the target, the errors of the imager, etc. Also, when the point of the needle disappears entering the body, no proper imagers are available to follow it in real time. This is because that "good" (i.e., geometrically consistent, high soft tissue image quality) imagers are not real time, and vice versa. As the distal support or nozzle thereof of the present invention holds the direction of the needle and measures the interaction of the needle with the tissues, this can be utilized to provide real-time information regarding the direction of needle deflection, which in turn can be used as a feedback for corrections by accordingly positioning and orienting the needle. The following describes the various features of the medical instrument driver 100 of the present invention in more detail.

As show in FIG. 1A, the medical instrument driver 100 is configured and arranged with the needle 20 positioned in from of the RCM module 10 so that the RCM base angle is set to γ=0° as shown in FIG. 1C. To gain distance between the RCM and the patient, the RCM module is initially inclined with 30° and operated about the $j_{10}=-30°$ central position. This is one more example of the flexibility of the RCM module in handling various end effectors.

In conventional needle drivers, the translational motion is traditionally created using slider joints. However, these mechanisms are longer than their stroke, as the driver is taller than the needle that it handles and thus limiting the applications of the driver in the tight space of medical imagers. The upper mechanism 110 of the medical instrument driver 100 of the present invention is configured and arranged so as to achieve near perfect linear motion using rotary joints, thus yielding a driver that is more compact as compared to prior art drivers. A simplified representation of the design and the schematic of the mechanism are presented in FIGS. 1E, F respectively.

As shown more clearly in FIGS. 1D, E the translational related structure of the upper mechanism 110 includes a crank member 112 (crank $P_1$-$P_2$), a rod member 114 (rod $P_2$-$P_4$), a plurality of pin joints $P_1$, $P_2$, $P_3$ (118a-c) and a slider joint $P_3$ (118d). The pin and slider joints 118a-d have normal intersecting axes. Near linear motion of the end point $P_4$ (needle head) 118c along the axis Y is achieved by optimizing the size of the mechanism. The size of an embodiment of the mechanism is given in the figure and it is within the skill of those knowledgeable in the art to scale for other max stroke values. The direct kinematics of the mechanism, describing the position of the needle point $P_5$ 119 in the XYZ coordinate system is a function of the crank angle u, is given in Equation 1, $$y_{(u)} = L_1\sin(u)\left(\frac{L_2}{(L_1\cos(u) - Z_1 + Z_2)\sqrt{1 + \frac{L_1^2\sin(u)^2}{\left(L_1\cos(u) - \atop Z_1 + Z_2\right)^2}}} - 1\right) + Y_1 - L_n$$

(Equations 1)

$$z_{(u)} = L_1\cos(u) - \frac{L_2}{\sqrt{1 + \frac{L_1^2\sin(u)^2}{(L_1\cos(u) - Z_1 + Z_2)^2}}} + Z_2$$

where, the dimension are given in FIGS. 1E,F. The inverse kinematics problem does not have a closed form solution, but can be easily solved with a numeric method such as Newton-Raphson, which converges in just a few (3-5) iterations.

Figure 2:
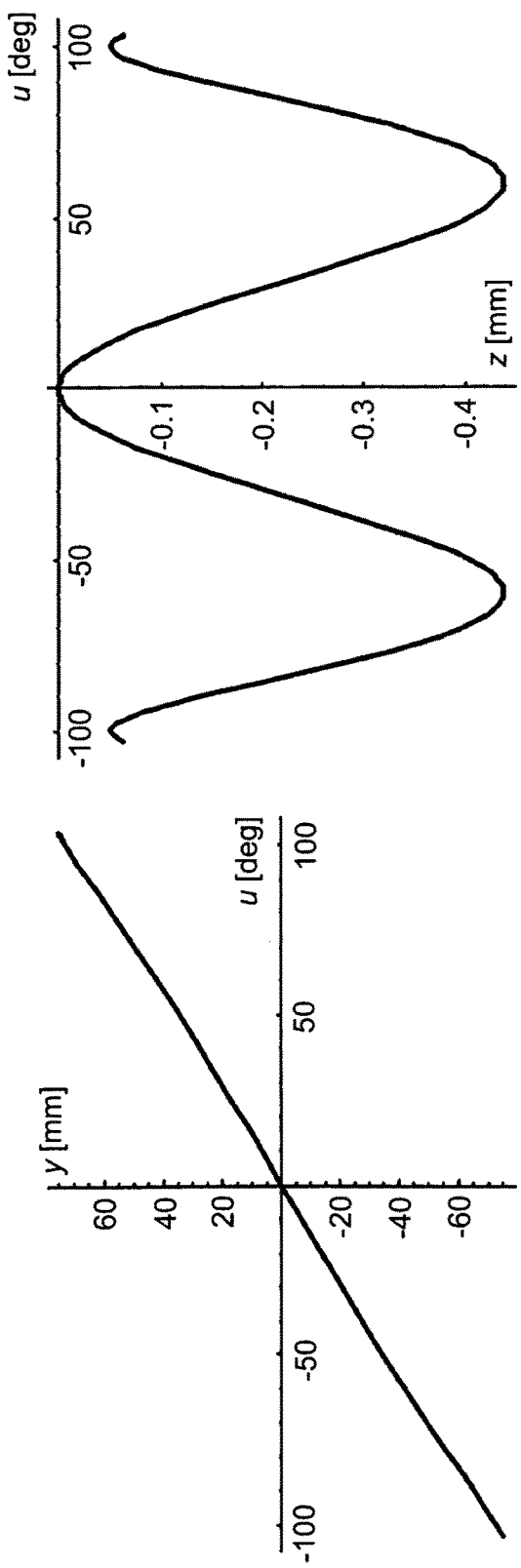
FIG. 2 contains graphical views showing Y and z coordinates of the needle point as a function of the driving crank angle u.

Graphically, the dependence of the y and z coordinates on the driving crank angle u is shown in FIG. 2. These plots show that the insertion is nearly linear with a small lateral displacement (<0.5 mm). The effect lateral displacement on the direction of the needle is further minimized by the needle guide of the nozzle.

The crank member 112 is driven by a servo motor 120 through a two stage transmission including a set of a bevel (2:1 transmission ratio) gear 122 and a spur (4:1) gear 124. Closed loop control is performed with feedback from a motor encoder, and a redundant encoder is custom constructed to "count" the teeth of the driving spur gear. This is constructed with two optical sensors (e.g., Omron EE-SPX842) mounted to give a quadrature encoded position signal over the gear teeth (e.g., Berg PFA 94-80, 80 teeth) in place of the encoder wheel. The redundant measurement provides a medical safety feature for this needle insertion axis.

When driven from the motor 120, the end point of the rod (point P4, 118c) moves along a quasi-linear trajectory, which drives the needle 20 by its head. However, the orientation of the rod member 114 with respect to the direction of needle insertion Y is variable. Thus, a parallel motion mechanism is provided to maintain the direction of the needle during insertion, as shown in FIG. 2.

Parallel mechanisms are typically implemented with parallelogram bar linkages, such as those used in the formerly ubiquitous universal drafting machines. In an exemplary illustrative embodiment, the medical instrument driver 100 uses a mechanism embodying two belts 130a,b, connected between equal pair pulleys 132 a-c at pin points P1-P2 and pin points P2-P4. Because the first pulley 132a is connected to the base of the medical instrument driver, the end pulley 132c maintains the same orientation (parallel mechanism) independent of the position of the needle insertion mechanism. The head of the needle 24 is then driven from the pulley 132c at pin point P4, which presents translational motion.

Figure 3A:
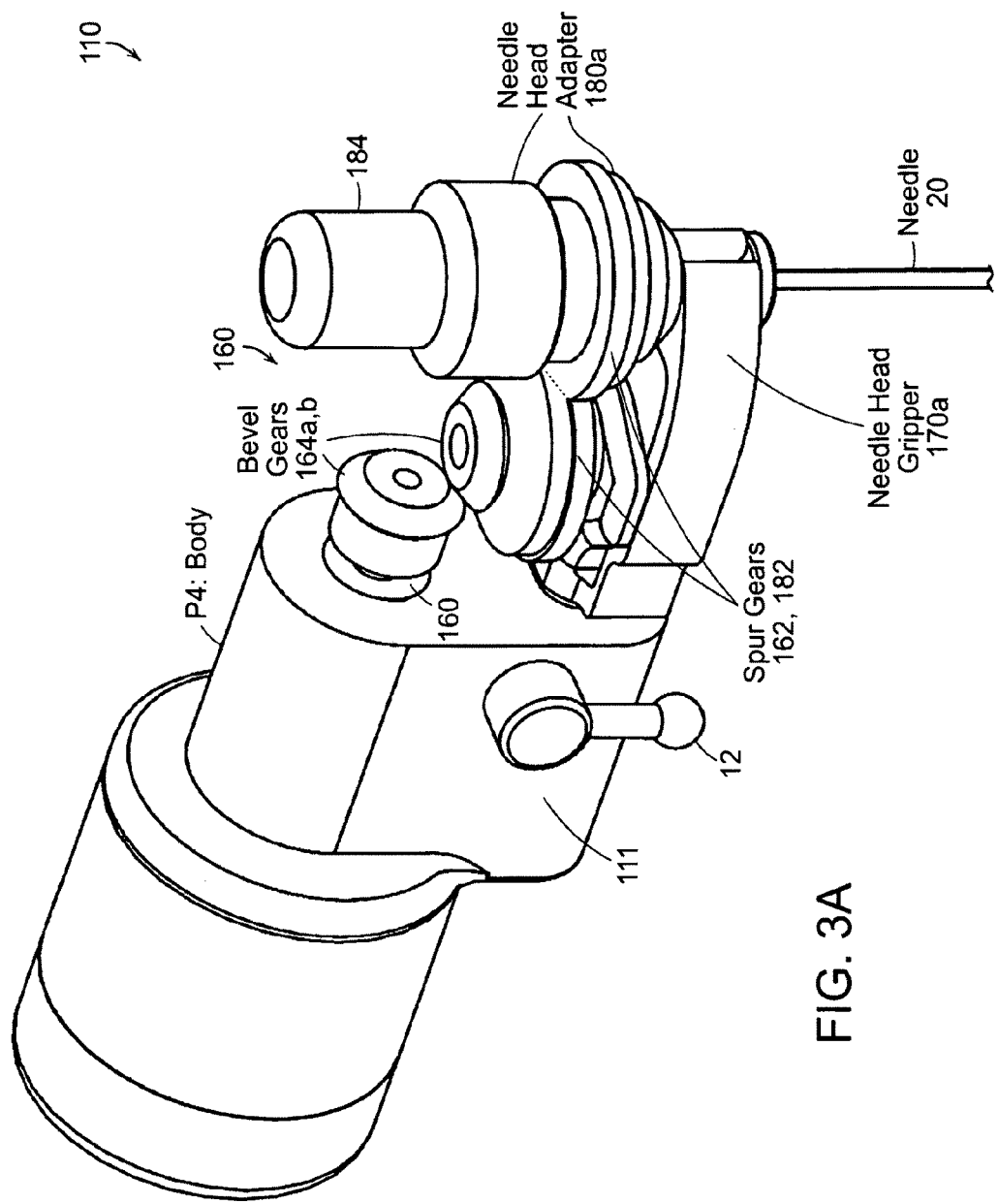
FIG. 3A is a perspective view showing the rotational structure of the upper mechanism of the medical instrument driver of FIG. 1A.
Figure 3B:
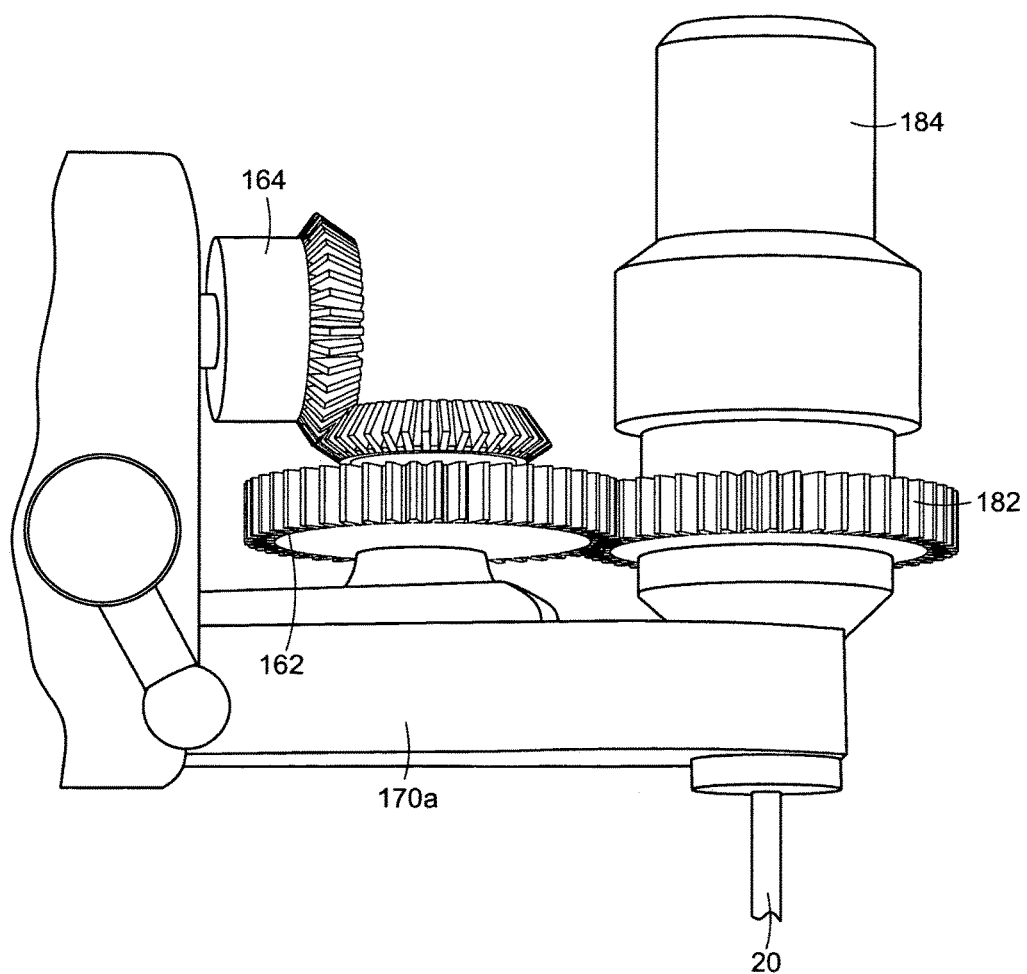
FIG. 3B is a side view of the rotational structure of FIG. 4B.

As described above, the upper mechanism 110 also includes a mechanism and/or structure that causes the needle 20 to rotate about the long axis of the needle, more specifically rotating the needle as the needle is being translated. In particular embodiments, and with additional reference to FIGS. 3A, B, the needle 20 is spun from its head through a gear transmission 160 built together with the upper gripper 170a, as shown in FIGS. 3A, B. The body 111 of the upper mechanism 110 is supported at P4 by the end of the parallel mechanism described above. As described herein, the head of the needle 20 is coupled to the needle head adapter 180a that includes a gear 182, e.g., a spur gear, that forms a part of the gear transmission 160.

A small size geared servomotor 166 is encased in the body 111 and rotates the needle 20 through the gear transmission 160. In exemplary embodiments, the first bevel gear 164a is driven by the motor 166, and the middle bevel gear 164b and the spur gears 162, 182 are connected to the gripper 180a. This construction allows the needle 20 to be released as described above and also allow the gripper 180a to be removed as discussed further below.

As indicated above, the medical instrument driver 100 of the present invention includes adapters 180a,b for releasably, operably coupling the needle 20 to the respective upper and lower mechanisms 110, 150 of the medical instrument driver. As also indicated above, such adapters 180a,b are used to accommodate various needle sizes, types and in the case of the upper or needle head gripper 180a to also mount a gear 182 at the head of standard needles.

Figure 4A:
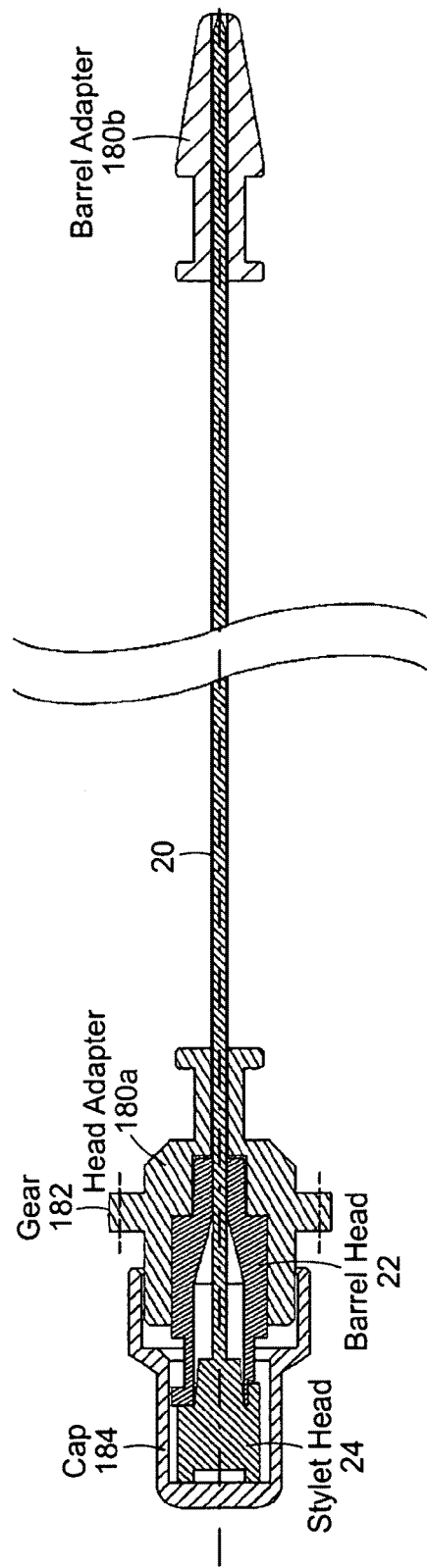
FIG. 4A is a cross-sectional view of a medical needle including first and second adapters according to the present invention.
Figure 4B:
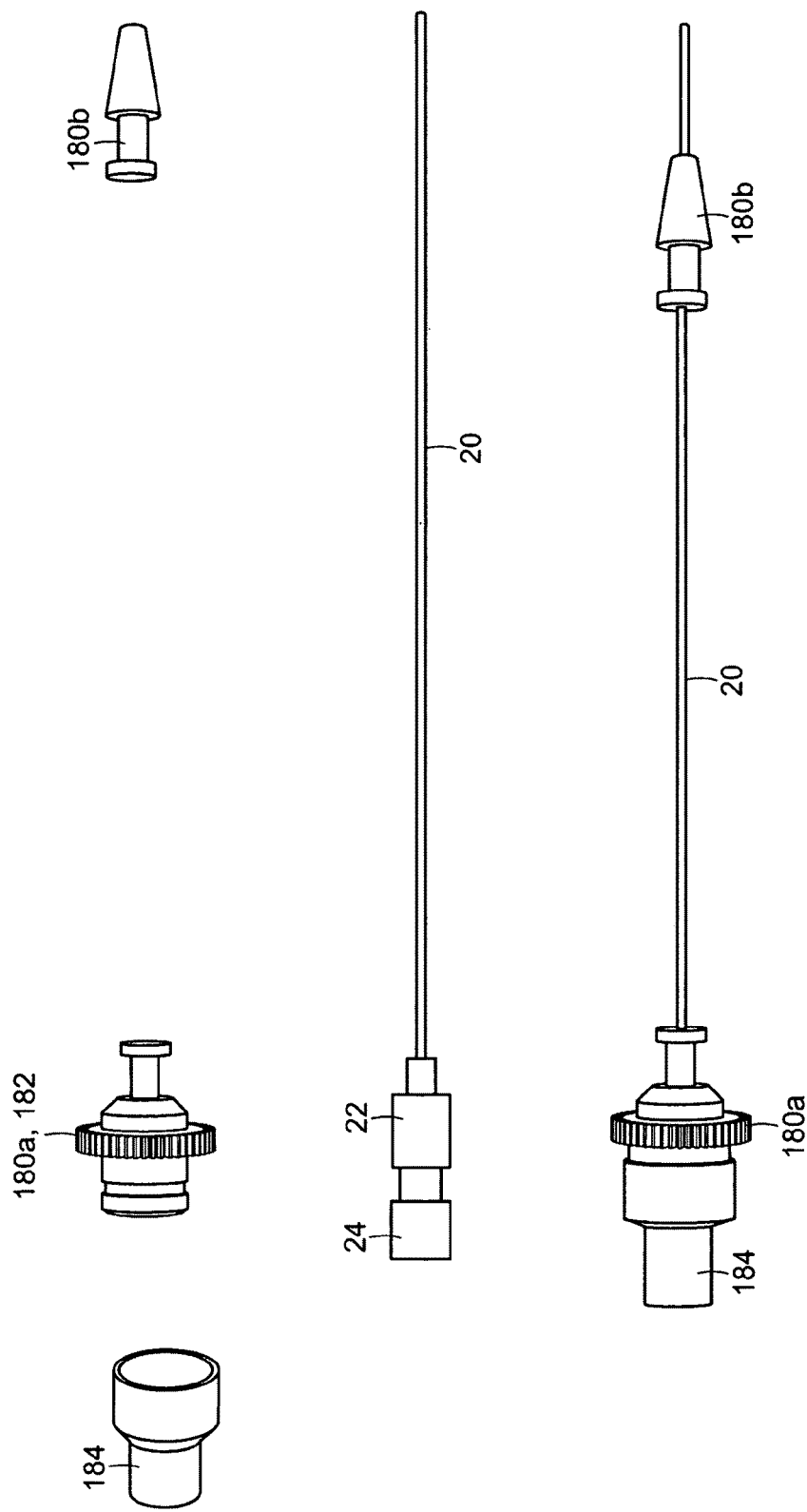
FIG. 4B are various pictorial views of the assembled medical needle of FIG. 3A and intermediary positions of such assembly.

Referring now also to FIGS. 4A, B there are shown a cross-sectional view of a medical needle 20 including first and second adapters 180a,b according to the present invention (FIG. 4A) and various pictorial views of the assembled medical needle of FIG. 4A and intermediary positions of such assembly (FIG. 4B). More specifically, in an illustrative embodiment there is shown an upper or needle head adapter 180a for a Cook DGB-18-15.0 needle. The gear 182 is part of the needle head adapter 180a and a cap 184 is included to lock the stylet 24. It is well within the skill of those knowledgeable in art to provide a needle head adapter for other needles, probes, or slender instruments. The lower or barrel adapter 180b generally depends on the diameter of the needle to match their bore an also so as to include a through aperture in which the needle 20 is slidably disposed.

In the case of probes or instruments having taller heads such as for example ablation probes, the needle head adapter 180a is adaptable or is configured and arranged so that the head of the needle 20 protrudes above the gear part 182 of the adapter. This design also allows direct access to the needle head as can be required for the clinical procedure such as the most common removal of the stylet. This also allows the needle to be accessed while it is mounted in the medical instrument driver 100.

Figure 5A:
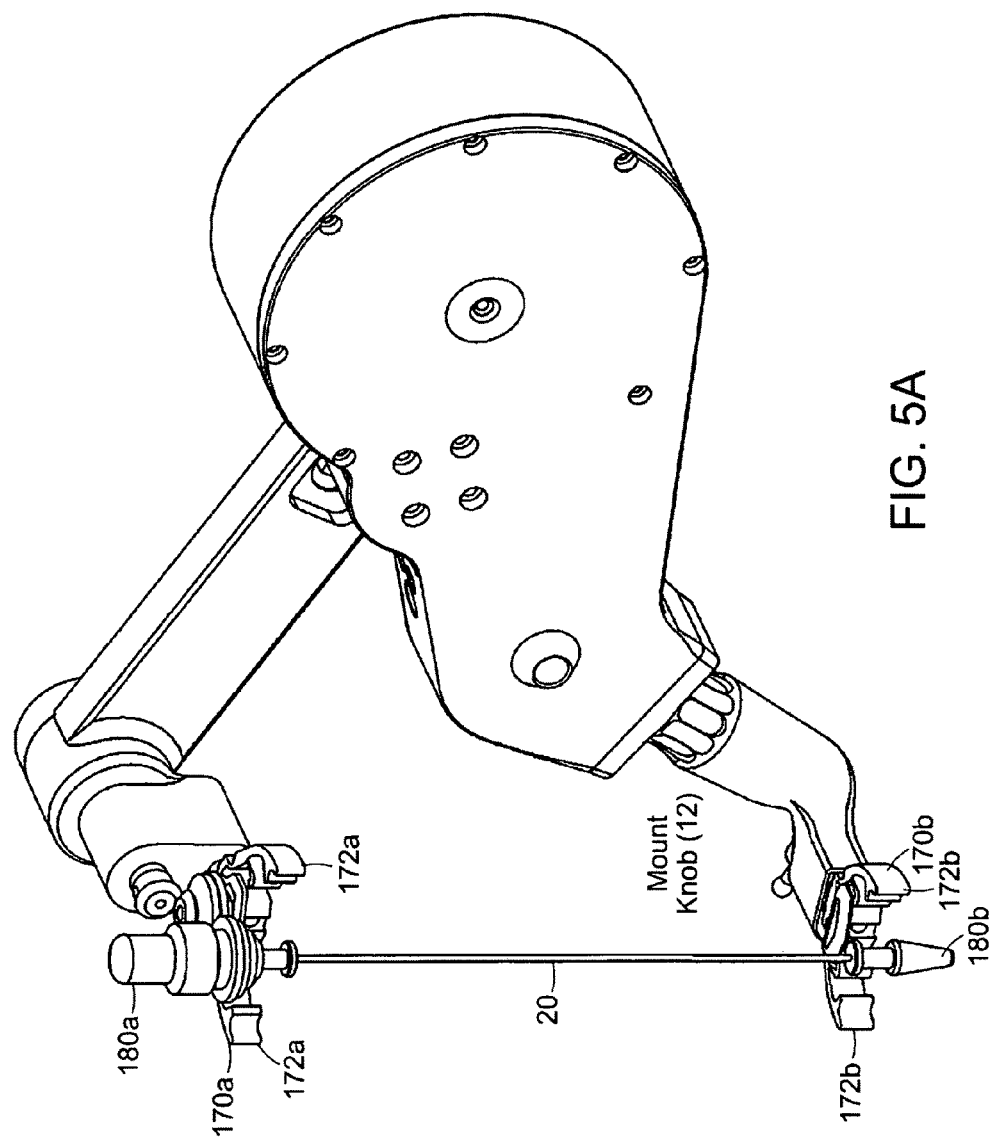
FIG. 5A is a perspective view of the medical instrument driver of FIG. 1A from a different perspective and showing the grippers in an open position.
Figure 5B:
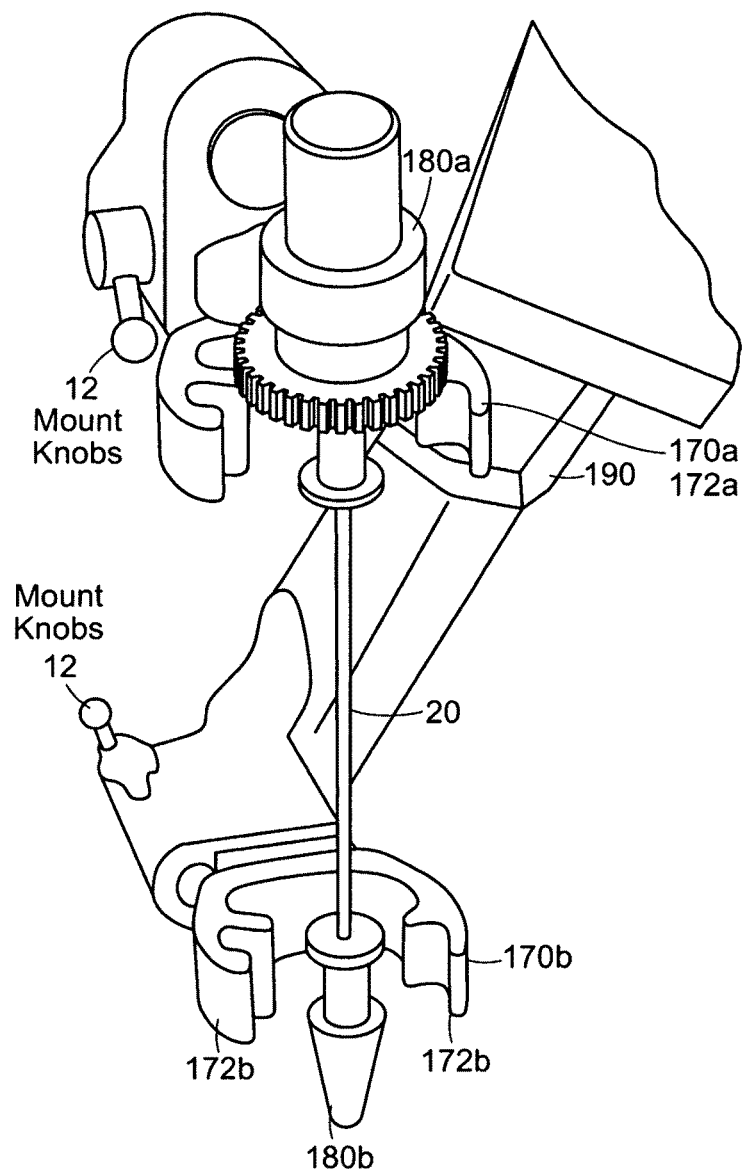
FIG. 5B is a pictorial view of the medical instrument driver depicted in FIG. 5A.
Figure 5C:
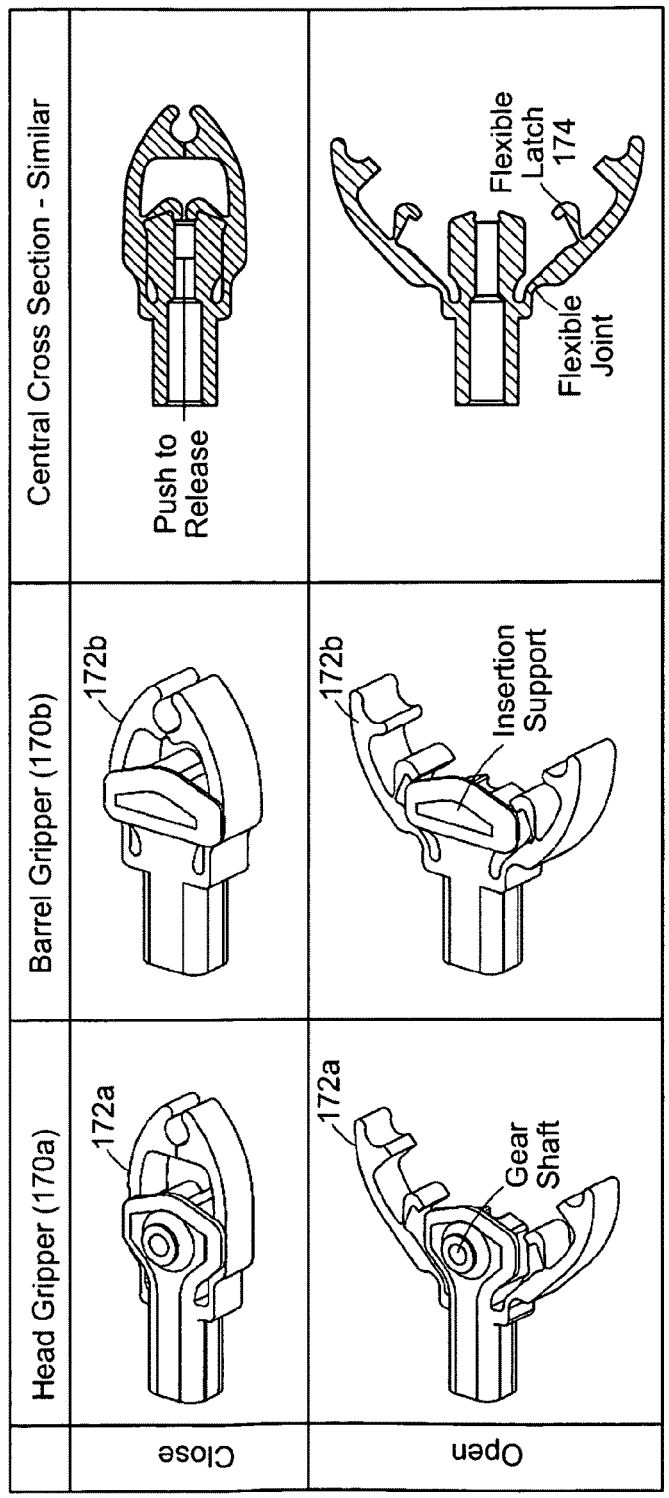
FIG. 5C includes various illustrative views of the head and barrel grippers in open and closed configurations and a central cross-section.

As indicated above, the medical instrument driver 100 of the present invention includes upper and lower grippers 170a,b which provide a mechanism for releasing the needle 20 quickly, automatically, and very smoothly, without moving or pushing it while also securing the needle for insertion. Referring now also to FIGS. 5A-C, there is shown a perspective view of the medical instrument driver 100 of FIG. 1A from a different perspective and showing the grippers 170a,b in an open position (FIG. 5A); a pictorial view of the medical instrument driver depicted in FIG. 5A (FIG. 5B) and various illustrative views of the head and barrel grippers 170a,b in open and closed configurations and a central cross-section (FIG. 5C).

As shown in FIG. 1A, the needle 20 is held by its adapters 180a,b in two grippers 170a,b at the head of the needle and in close proximity of the skin. The upper or head gripper 170a is configured so as to be operably coupled to rotational and translational structure so as to spin and insert the needle while the lower or barrel gripper 170b guides the needles direction.

In illustrative embodiments, each gripper 170a,b includes two finger-like arms 172a,b that clip (fasten) together for holding the respective needle adapter 180a,b and thus the needle 20, and which arms also swing aside to release the needle 20. When the grippers 170a,b are in the open position, such as shown in FIGS. 5A, B, the needle 20 is released and if another medical instrument or needle is intended for use, the user can insert the new medical instrument into the grippers and thereafter close the grippers so that the new instrument can be deployed by the medical instrument driver 100.

As indicated above, and as shown in FIG. 5C, the head and barrel grippers 170a,b can have similar designs, with the basic difference being that the head gripper 170a also is configured so it also carries certain of the gears (the central gears) of the gear transmission 160 which is part of the rotational structure or mechanism for spinning the needle 20 (e.g., see FIGS. 3A,B). In illustrative exemplary embodiments, the grippers 170a,b have a one piece construction and are made of a material appropriate for the intended use. In an illustrative embodiment, the grippers are made of plastic, such a Delrin.

As indicated above, mounting the needle 20 is a process that is done manually and is accomplished by manually closing the fingers after the needle and the related adapter are appropriately disposed therein. Also, while the release is actuated by a common mechanical command that simultaneously releases all 4 fingers of both grippers 170a,b. In an exemplary illustrative embodiment, such release is performed by pneumatically actuating the grippers, but this is not limiting as it is within the scope of the present other for any other types of actuation or actuation mechanisms to be used.

In illustrative exemplary embodiments, the two fingers 172a,b of the grippers 170a,b as well as their respective latches are articulated on flexible joints. In this exemplary embodiment of a two finger design, with the described lateral opening, the two fingers are moved well away from the needle and the associated adapter without forcing it. This is advantageous from the viewpoint of the precision and safety of the clinical procedure, as well as making sure that the release action does not influence the position of the needle, but rather it smoothly lets go of the needle/adapter.

In use, the medical instrument driver 100 of the present invention is covered, for example, with a sterile bag that can also cover the other parts of a robotic system such as a RCM module 10. The sterile components typically are the end parts that are in contact with or in direct proximity of the needle and which can include the needle 20, its adapters 180a,b, and the two grippers 170a,b, where the head gripper 170a would also include the middle gears of the gear transmission 160. Thus, these functionalities are typically constructed of materials that are appropriate for the intended use such as, for example, metal (stainless steel) for the needle and plastic for the other functionalities. It also is within the scope of the present invention for the medical instrument or needle to be manufactured so as to include one or both of the upper/head adapter 180a and the lower/barrel adapter 180b. In further embodiments, the grippers 170a,b pierce through the sterile bag and are mount in the robot or robotic arm using two eccentric locks, by turning the mount knobs 22.

As indicated above, the medical instrument driver 100 of the present invention further includes sensors 190 a,b, more particularly, one or more sets of torque/force sensors 190a,b to measure (a) the interaction force of the nozzle 152 with the patient and (b) the force of needle insertion. In an illustrative exemplary embodiment, the medical instrument driver 100 embodies two sensors 190a,b. One sensor(s) 190b, a force sensor, is arranged so as to measure the interaction between the nozzle of the needle and the skin in three component direction and the other sensor(s) 190a is arranged so as measure the axial force of needle insertion with a built in custom torque sensor (e.g., Full-Bridge Thin-Beam Load Cells, Omega LCL-005) measuring the drive of the motor 120 for the needle insertion or needle translation mechanism.

As is known to those skilled in the art, the torque sensor 190b is located so as to be operably coupled to the mechanical linkage used to translate the needle into the tissue. Alternatively, and as known to those skilled in the art, the torque being developed can be derived by measuring the current flowing to the electrical motor 120. In more particular embodiments, the torque sensor 190a is located in proximity to the motor 120 and downstream of the gearing contained within the motor.

The axial force along the needle is calculated by sensing the torque applied to the mechanism driving the upper arm of the needle. This torque is then converted to a force along the needle direction by accounting for the kinematics of the drive train mechanism. There is some noise from friction in this measurement, but, it has been observed that this capability provides a reasonable representation of the actual force.

Figure 6A:
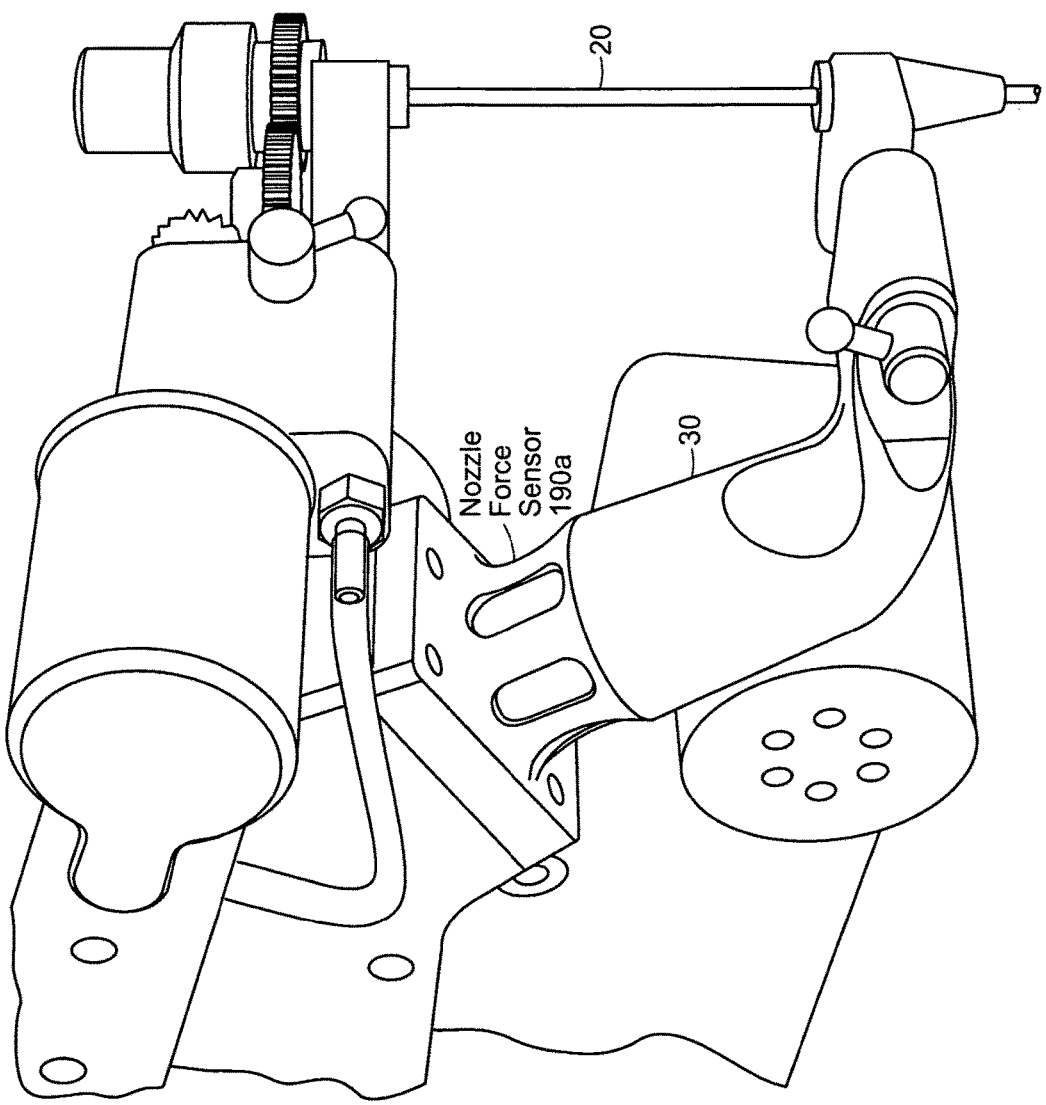
FIG. 6A is a perspective view of a medical instrument driver according to the present invention when configured with a nozzle force sensor(s).
Figure 6B:
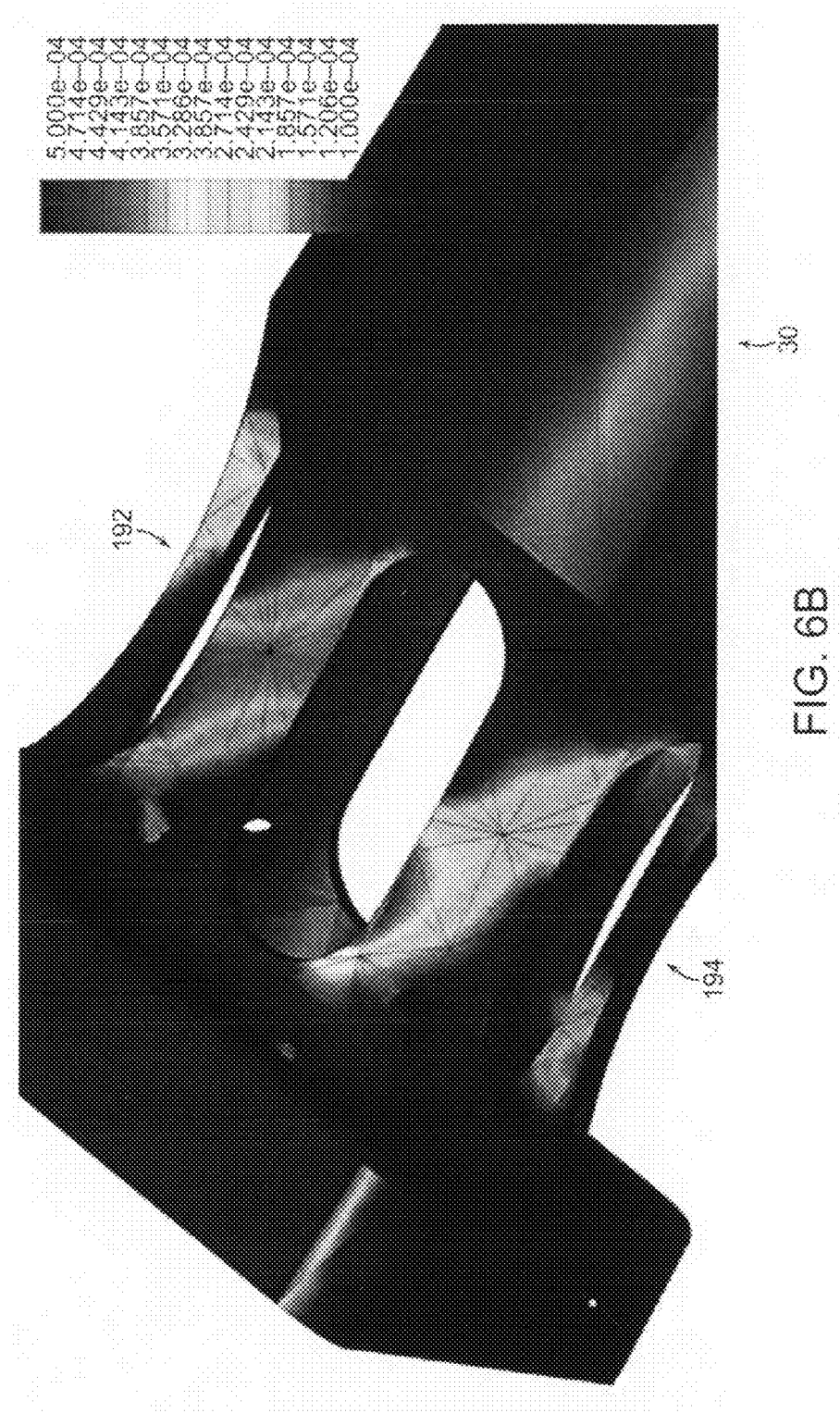
FIG. 6B is an pictorial view of the geometric element modeling design.

Referring now also to FIGS. 6A, B, there is shown a perspective view of a medical instrument driver 100 according to the present invention when configured with a nozzle force sensor (FIG. 6a) and a pictorial view of the geometric element modeling design (FIG. 6B). In an illustrative exemplary embodiment, the nozzle force sensor 190b is built into a lower arm 30 that supports the lower/barrel gripper 170b. In illustrative embodiments, six windows 192 were modeled at the base of this arm 30 to concentrate the stress over 6 bridges 194 and six identical strain gauges (e.g., HBM 1-LY13-3/120) are used to measure the corresponding strains (see FIG. 6B). The geometry, size, and position of the bridges has been modeled and optimized using Geometric Element Modeling (GEM similar to FEM) methods in Pro/Engineer so that the strains in the bridges match the characteristics of the strain gauges when 0-50N forces are applied at the nozzle point in the XYZ directions of the medical instrument driver coordinate system as illustrated in FIG. 1A.

The transfer function between the 6 dimensional (6D) strain space and the 3D space of forces is chosen as:

$$\vec{F}_{[3\times 1]} = K_{[3\times 6]} \vec{X}_{[6\times 1]} \quad \text{(Equation 2)}$$

where, the calibration matrix K between the nozzle point forces $\vec{F}$ and the strain vector $\vec{X}$ is determined using a linear least-squares method over a set of m≥6 calibration experiments:

$$F_{[3\times m]} = K_{[3\times 6]} X_{[6\times m]} \quad \text{(Equation 3)}$$

With a Singular Value Decomposition of the strain matrix X for example, the solution K is given by:

$$F = K \cdot U \cdot [\text{diag} W] \cdot V^T$$

$$K = F \cdot V \cdot [\text{diag} W]^T \cdot U^T \quad \text{(Equation 4)}$$

With GEM simulated data the calibration errors are on the order of 0.01% measured on norm. The experimental calibration of the sensor is facilitated by the RCM orientation module supporting the medical instrument driver, which can precisely change the orientation of the needle nozzle. Thus, the nozzle sensor 190b can be calibrated against a simple scale. The nozzle is pressed against the scale to various loads (1-25N performed) and at various RCM angles spanning the motion envelope. The components of the force F are determined by projecting the scale reading on the XYZ coordinate system according to the inclination angles of the RCM (Rx, Rz shown in FIG. 1A). The corresponding strain vector $\vec{X}$ is read from the gauges. Experimentally, the sensor 190b was successfully calibrated with less than 5% norm errors.

As indicated above, in further aspects of the present invention there is featured a system or apparatus for inserting such a medical instrument, where such an apparatus includes any of a number of robotic systems including image-guided robotic systems, known to those in the art or hereinafter developed, and configuring or adapting such a robotic system so that the medical instrument driver of the present invention is used in combination with such a robotic system.

Figure 7:
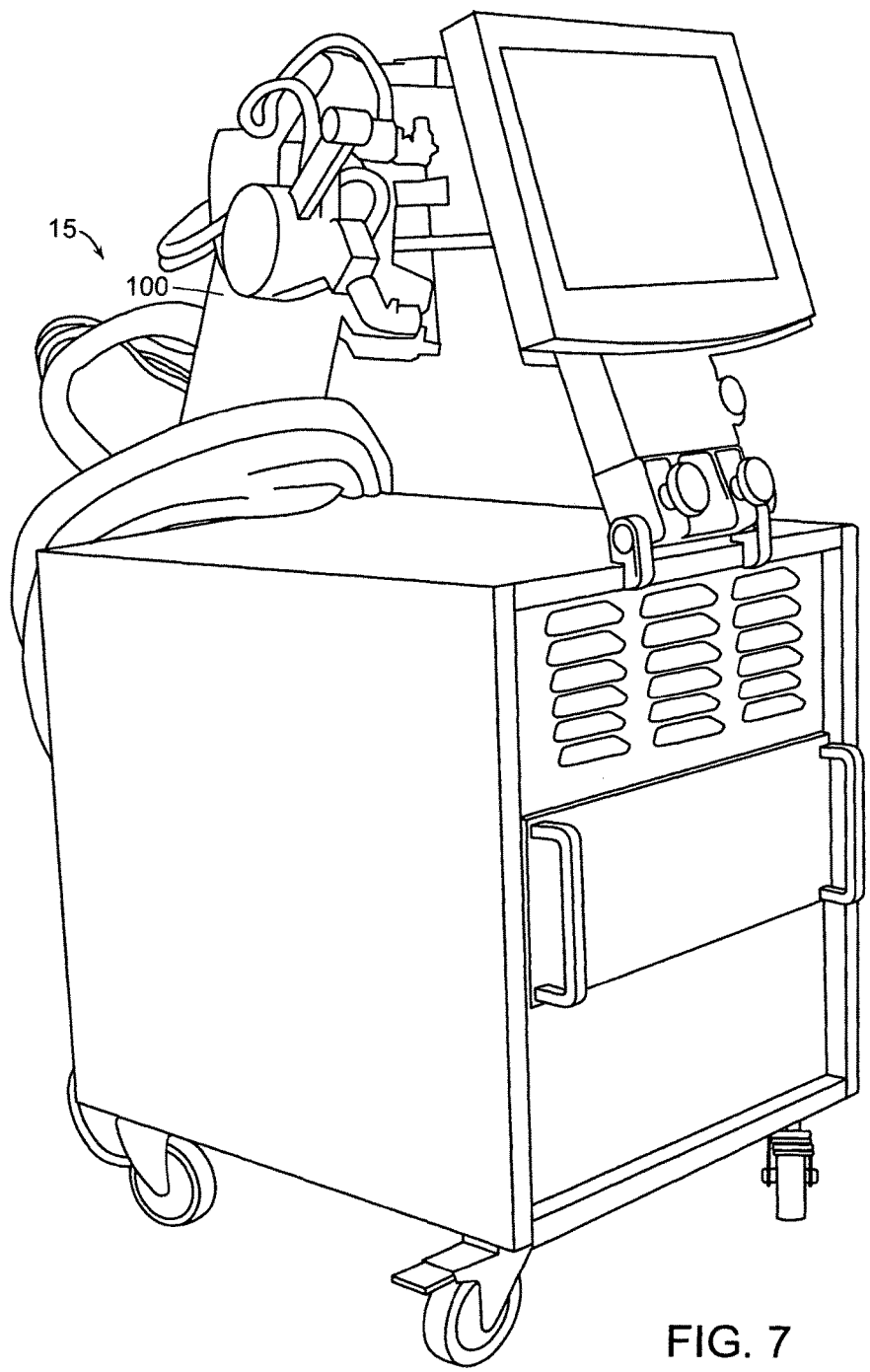
FIG. 7 is a pictorial view showing the medical instrument device in combination with a robotic system.

In a particularly illustrative exemplary embodiment, there is shown in FIG. 7, a robot 15 such as an AcuBot robot as is known to those skilled in the art, adapted so as to include a medical instrument driver 100 in place of a PAKY needle driver. This pictorial view shows the AcuBot robot in the transport position and attached to the top of its control cabinet.

Figure 8:
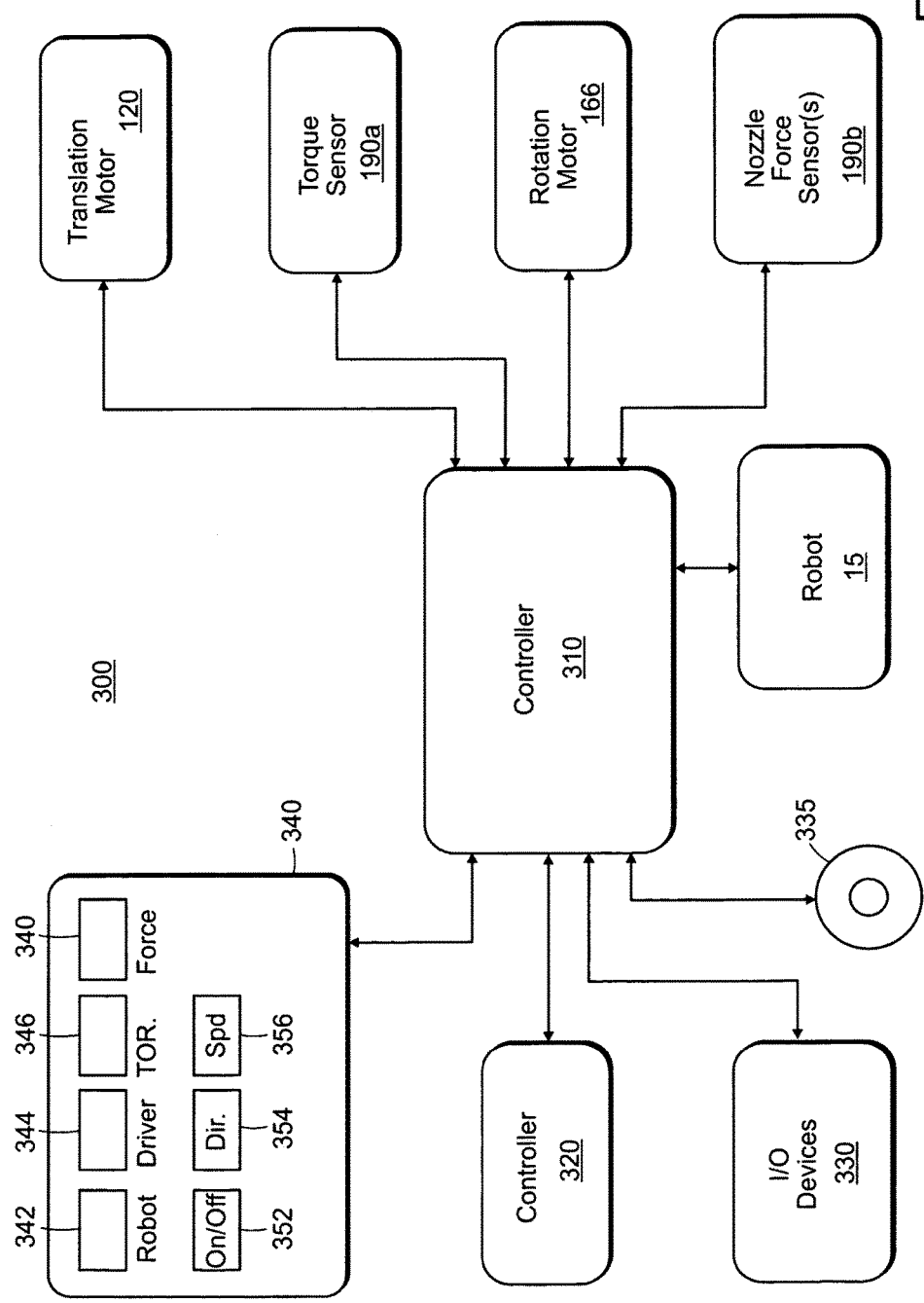
FIG. 8 is a block diagram view of a control system that controls functionalities of a medical instrument driver and robot.

The operation of the medical instrument driver 100 alone or in combination with a robot 15 can be best understood with reference to the control system 300 shown in FIG. 8 and with reference to FIGS. 1-7 described above. Such a control system 300 includes a controller 310 that is operably coupled to functionalities of the medical instrument driver 100, functionalities of the robot 15, a display 320, I/O device(s) 330, and a device input panel 340.

The controller 310 is any of a number of devices known to those skilled in the art which can control these functionalities and otherwise carry out the commands and signal processing necessary to control the functionalities, monitor input parameters, provide outputs of monitored parameters and/or take actions responsive to out of normal conditions. In-particular exemplary embodiments, the controller 310 includes processing circuitry (e.g., microprocessor, ASIC), memory used by the processing circuitry (RAM), storage memory for storing programs or applications used to carry out the functions of the controller (e.g., flash or spindle memory devices) as well as interfaces for operably coupling the controller 310 to each of the functionalities (e.g., motors 120, 166) connected thereto.

The display 320 is any of a number of devices known to those skilled in the art and hereinafter developed that display information responsive to signals outputted by a controller 310 or the controller interface(s). Such displays include LCD displays, CRT and plasma displays. The I/O device(s) 330 are any of a number of devices known to those skilled in the art by which a user can update database(s) or programs/applications embodied in the controller and/or stored in the storage memory and otherwise communicate with the processing circuitry. In illustrative embodiments, such I/O devices 330 include a keyboard and mouse.

Also included is a joystick 335, that is operably and communicatively coupled to the controller 310. The joystick 335 is any of a number of I/O devices known to those skilled in the art, which output signals representative of the movement of the stick with respect to the base thereof. The use of the joystick 335 in combination with the controller 310 is discussed further below in connection with the device input panel 340. As is known to those skilled in the art, other devices known in the art can be adapted to perform the functions of the joystick.

As indicated above the controller 310 is operably and communicatively coupled to the translation motor 120 that causes the needle 20 to translate and the rotational motor 166 that rotates the needle. The controller 310 outputs signals to each of these motors 120, 166 so as to control the operation of each motor, including signals that for example, instruct the motor which direction the motor is to rotate in (e.g., clockwise or counterclockwise); set the speed of rotation for a motor, provide instructions as to the number or rotations or partial rotations of the motor and stopping the motor functions when a desired condition is obtained or when an out of normal condition is sensed. For example, the controller 310 can control operation of the motor responsive to signals from an encoder that represent an amount of rotation of the motor.

As indicated above, the controller 310 is operably and communicatively coupled to the torque sensor 190a and the nozzle sensor(s) 190b, so as to receive input signals from each of these sensors. In more particular embodiments, the controller 310 processes these signals to provide outputs of measured parameters, to adjust operation of the translational or rotational motors 120, 166 and/or to take such other actions when out of normal conditions are being experienced.

The device input panel 340 provides a mechanism by which a user can input parameters and/or commands to the controller so as to thereby control operation of the robot 15 including the functionalities thereof and/or the medical instrument driver 100. Although the input panel 340 is illustrated as a separate device, this shall not be considered limiting as it is which the skill of those knowledgeable in the art to adapt other devices including the display 320 so as to carry out the functions of the device input panel. For example, the display 320 can be configured and arranged so that a touch screen or light pen function is available whereby the user can provide inputs using such functions. Also, the reference to buttons in the following discussion shall not be interpreted as being limited to mechanical switches but also include buttons or other artifacts that can be shown on a display or panel that are selectable using other techniques or mechanisms known to those skilled in the art.

The device input panel 340 includes two buttons 342, 344 that control which device is under control of the joystick 335. If the robot button 342 is selected, signals representative of the movement of the joystick 335 are outputted by the controller and communicated to the robot 15 and in turn additional signals are outputted within control circuitry of the robot so as to control the functionalities of the robot. In particular embodiments, the signals from the joystick 335 control the robot 15, and in particular the robot arm 10, so that the medical instrument driver 100 is moved and positioned so the needle 20 is proximal the tissue and oriented to aim at the target area. Preferably when the robot button is selected, the controller 310 also takes actions to in effect lock out operation of the medical instrument driver 100 so that the needle 20 is not moved by the driver during movement of the robot.

If the medical instrument driver button 344 is selected, then the controller 310 is configured so as to control operation of the medical instrument driver 100. Preferably when the driver button 344 is selected, the controller 310 also takes actions to in effect lock out operation of the robot 15 so that the robot including the robot arm does not move, while the needle is being deployed into the tissue. In this operational mode, the movement of the joystick 335 is used by the controller to output signals to the translation motor 120 as well as other functionalities of the medical instrument driver. For example, the joystick 335 can be used to control the translation movement of the needle into or out of the tissue so that, for example, movement of the joystick in one direction causes the controller to output signals to the translation motor 120 thereby causing the translation motor to rotate in a given direction which in turn cause the needle 20 to translate in the desired direction.

As indicated above, the torque sensor 190a and force sensors 190b are each operably and communicatively coupled to the controller 310. In particular embodiments, the controller 310m processes these input signals and causes the determined torque to be displayed on an output screen 346 and causes the determined nozzle force to be displayed on an output screen 348. As also indicated herein, the controller 310 also can use the determined torque and nozzle force(s) to determine if protective actions should occur, for example, with regard to translation and/or rotation of the needle. In illustrative examples, the controller 310 can terminate translation or rotation, causing the needle to be withdrawn or increase/decrease rotational speed of the needle.

As to needle rotation, the device input panel 340 further includes buttons 352, 354, 356 that control operation of needle rotation. An on/off button 352 is provided that controls operation of the rotational motor 166 such that such rotation cannot occur until the user provides a signal to the controller so it is configured to allow such motion. For example, in illustrative embodiment, the controller 310 is configured so that when the button 352 is in the "on" position the needle is rotated until the button is actuated to turn it off. In another illustrative embodiment, the controller 310 is configured so that when the button 352 is put into the "on" position the needle 20 is rotated only when the needle is being translated and not rotated when the needle is not being translated. In yet further embodiments, the user can set the button 352 in the "off" position so that needle rotation is off when the user wants to only translate the needle.

The device input panel 340 also includes a button 354 for controlling the direction of rotation of the rotational motor 166 and a button 356 for controlling the rotational speed of the needle to one of a plurality of rotational speed. The direction button 354 allows the user to control which direction (clockwise, counterclockwise) the needle is to be rotated so that for example, the needle rotates in a clockwise or counter clockwise direction when the needle is being translated in a particular direction. For example, when inserting the needle 20, the user could set a clockwise direction of rotation so that the needle spirals in a clockwise direction when it is being inserted and when it is being withdrawn, the user could set a counterclockwise direction of rotation so that the needle spirals in a counterclockwise direction when being withdrawn.

As indicated herein, it is desirable to have the capability to rotate the needle at one of a number of different speeds while the needle is being inserted and/or withdrawn. Thus, the speed button 356 provides the mechanism by which the user can select the desired rotational speed for the needle such that the controller 310 thereafter controls the rotational motor 166 such that the desired rotational speed is obtained. In further embodiments, the user can adjust the needle rotational speed during the needle insertion/withdrawal process for example, responsive to signals or indicators that such a speed adjustment may be desirable. In illustrative embodiments, the rotational speed can be set to one of the three different rotation speeds: 0, 90, or 180 rpm.

Example 1

A study was undertaken to evaluate two features of a new rotating needle driver in a domestic swine model: (1) a quick release safety mechanism and (2) the impact of spinning the needle on the force profile.

Materials and Methods

The robotic system used in these experiments is an updated version of the "AcuBot" system built by the Urology Robotics Laboratory at Johns Hopkins Medical Institutions. The original AcuBot included the "PAKY" (Percutaneous Access of the KidneY) needle driver, the "RCM" (Remote Center of Motion) orientation module, and joystick control. A three degree of freedom Cartesian stage, passive positioning S-arm, and "bridge frame" enable the system to achieve a compact and flexible design for interventions at multiple points along the body.

A compact medical instrument driver (RND) was provided that holds the needle from two points for enhanced support and accurate insertions. This design prevents buckling of long thin needles. Moreover, it is capable of spinning the needle during insertion in either direction.

A custom force sensor was built into the lower arm that holds the nozzle and the mechanical structure of the lower arm was machined so that it deflects very slightly when any force is applied to the nozzle holding the needle. Strain gages were mounted on the lower arm to sense this deflection. Through a calibration process and calibration matrix, the output of these strain gages is converted into three orthogonal forces at the nozzle tip. Therefore, this force sensing capability measures the interaction between the needle shaft and the surrounding tissue.

The RND also can measure the axial force along the needle. This force is calculated by sensing the torque applied to the mechanism driving the upper arm of the needle. This torque is then converted to a force along the needle direction by accounting for the kinematics of the drive train mechanism. There is some noise from friction in this measurement, but by pressing manually along the direction of the needle and observing the reported force, it has been observed that this capability provides a reasonable representation of the actual force.

A safety mechanism was built into the needle driver to release the needle which can be triggered manually or upon a desired force level measured by the force sensors. The needle is quickly released from the two grippers, one at the head of the needle and one close to the skin. The gripper at the head of the needle controls the spin and inserts the needle while the second gripper, close to the skin, guides its direction. Both grippers were fabricated from Delrin plastic and were designed to include two finger-like arms which clip together to hold the needle and swing aside during release. These grippers are low cost and can be easily manufactured to accommodate standard needle sizes.

Experiments to test the AcuBot1 V2-RND system were performed on domestic swine in a multi-modality interventional suite, specifically designed for translational and pre-clinical evaluation of image-guided devices. A domestic swine (100-125 lbs) was initially sedated with a mixture of ketamine, xylazine, telazol, and butorphanol, then intubated and maintained under general anesthesia with isofluorane. After the animal was placed supine on the CT table, the AcuBot1 system was mounted onto the table using a custom designed mount and "bridge frame". A preliminary CT scan was obtained to determine the location of the target in the liver. For each insertion, a different target and skin entry point were determined by the physician. The physician then marked the skin entry point on the pig. After proper securing of an 18 gauge 15 cm Diamond GREENE tip (COOK Biotech) needle within the needle driver, the robotic arm was positioned directly over the marked skin entry point.

The control parameters were then set to one of the three different rotation speeds: 0, 90, or 180 rpm. While other literature has published work with max spin values up to 2,000 rpm, for this system the maximum spin is 180 rpm. This was chosen to be the maximum rotation speed and an intermediate rotation speed of 90 rpm also was selected. At each of these speeds 6, 7, and 3 needle insertions were performed respectively. The physician also created a small incision at the marked point to facilitate needle advancement. This is not a standard practice in the clinical setting, however, due to the thickness of porcine skin as compared to human skin, this was necessary to allow the needle to be inserted. The physician used the joystick to drive the needle towards the target and the control software of the robot recorded the needle insertion depth and forces in the X, Y, and Z directions for analysis as described later.

Results

A total of 16 insertions, 14 in liver and 2 in lung, were performed. The two lung insertions were performed to see if there was a difference with the needle driver performance between lung and liver. There was no significant difference in the two lung trials and the liver trials. Nonetheless, of these insertions 12 released completely upon the desired set force and four failed. Two of the four failures were released before reaching proper depth during insertion and two did not release at all. Needle release prior to achieving proper depth was due to the needle interaction with more compact tissue, specifically muscle. Though the experiments were not explicitly designed to evaluate sensitivity of the force measures, these two failures suggest that the quick release mechanism should be adjusted to account for tissue variation based on CT image data. Other models to determine force profiles for this safety mechanism are being investigated. The other two failures that did not release were primarily due to excessive use and deterioration of the Delrin grippers. However, in the clinical setting, this would not be an issue because such low cost, easily manufactured parts can be disposed of after a certain number of insertions.

Data accumulated during the experiment also shows the potential for needle rotation to reduce insertion force.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A medical instrument driver for causing a medical instrument to be inserted into tissue of a patient, comprising:
an upper mechanism having a translation and rotational mechanism operably coupled to a proximal portion of the medical instrument, the translation and rotational mechanism including:
a translation structure being configured to translate the medical instrument along a long axis of the medical instrument responsive to rotational movement of an end of such structure, and a rotational structure configured to rotate the medical instrument about the long axis as the medical instrument translates along the long axis; and a lower mechanism having a distal support that is distal from the translation and rotational mechanism, the distal support having an aperture in which a distal portion of the medical instrument is slidably disposed, wherein the distal support and the translation and rotational mechanism are arranged such that the distal portion of the medical instrument moves through the aperture, and an insertable end of the medical instrument exits the aperture and is capable of being inserted into the tissue of the patient, during insertion of the medical instrument into the tissue, the upper mechanism moves along the long axis while the lower mechanism remains substantially fixed, thereby limiting movement of the medical instrument in a plane perpendicular to the long axis during the insertion, and the translation structure includes: a crank member disposed between a first rotary joint and a second rotary joint, a rod member extending between the second rotary joint and a fourth rotary joint, where the fourth rotary joint is operably coupled to the medical instrument, and a slider joint that is slidably coupled to the rod member and is disposed between the second and fourth rotary joints.

2. The medical instrument driver of claim 1, wherein the translation and rotational structures cooperate so that the medical instrument spirals into the tissue.

3. The medical instrument driver of claim 1, wherein the translation structure includes a plurality of rotary joints.

4. The medical instrument driver of claim 3, further comprising a motor operably coupled to the first rotary joint such that rotation of the motor drives the crank member so that rotation of the motor also thereby causes an end point of the rod member to move essentially along a linear trajectory.

5. The medical instrument driver of claim 4, wherein the translation structure further includes a plurality of pulleys disposed at each of the first, second and fourth rotary joints and first and second belt members, where the first belt member is arranged so as to extend between the pulleys at the first and second rotary joints and the second belt member is arranged so as to extend between the pulleys at the second and fourth rotary joints.

6. The medical instrument driver of claim 1, wherein the rotational structure includes a drive motor and gears that are arranged so as to operably couple the medical instrument and the drive motor.

7. The medical instrument driver of claim 1, further comprising at least one sensor configured and arranged for measuring a force between the distal support and the patient and a force of needle insertion into the tissue.

8. The medical instrument driver of claim 1, wherein the upper mechanism and the lower mechanism are arranged such that at least a portion of the upper mechanism and at least a portion of the lower mechanism are positioned along the long axis of the medical instrument.

9. An apparatus for causing a medical instrument to be inserted into tissue, said apparatus comprising:

a robotic device having an arm that is movable in one or more dimensions;

a medical instrument driver operably coupled to the medical instrument and operably coupled to the robotic arm, wherein the robotic arm is movable so as to position the medical instrument driver with respect to a target area, wherein said medical instrument driver includes:

an upper mechanism having a translation and rotational mechanism operably coupled to a proximal portion of the medical instrument via a proximal portion of the robotic arm, the translation and rotational mechanism including:

a translation structure being configured to move the medical instrument along a long axis of the medical instrument responsive to rotational movement of an end of such structure, and a rotational structure configured to rotate the medical instrument about the long axis as the medical instrument moves along the long axis; and a lower mechanism having a distal support operably coupled to a distal portion of the robotic arm and which is distal from the translation and rotational mechanism, said distal support including an aperture in which a distal portion of the medical instrument is slidably disposed, wherein the distal support and the translation and rotational mechanism are arranged so the distal portion of the medical instrument moves through and exits the distal support through the aperture such that an insertable end of the medical instrument is capable of being inserted into the tissue of the patient, during insertion of the medical instrument into the tissue, the upper mechanism moves along the long axis while the lower mechanism remains substantially fixed, thereby limiting movement of the medical instrument in a plane perpendicular to the long axis during the insertion; and the translation structure includes: a crank member disposed between a first rotary joint and a second rotary joint, a rod member extending between the second rotary joint and a fourth rotary joint, where the fourth rotary joint is operably coupled to the medical instrument, and a slider joint that is slidably coupled to the rod member and is disposed between the second and fourth rotary joints.

10. The apparatus of claim 9, wherein the translation and rotational structures cooperate so that the medical instrument spirals into the tissue.

11. The apparatus of claim 9, further comprising a motor operably coupled to the first rotary joint such that rotation of the motor drives the crank member, where such rotation of the motor also thereby causes an end point of the rod member to move essentially along a linear trajectory.

12. The apparatus of claim 11, wherein the translation structure further includes a plurality of pulleys disposed at each of the first, second and fourth rotary joints and first and second belt members, where the first belt member is arranged so as to extend between the pulleys at the first and second rotary joints and the second belt member is arranged so as to extend between the pulleys at the second and fourth rotary joints.

13. The apparatus of claim 9, wherein the rotational structure includes a drive motor and gears that are arranged so as to operably couple the medical instrument and the drive motor.

14. The apparatus of claim 9, further comprising a first adapter and a second adapter, wherein the first adapter is configured to operably couple the medical instrument to the translation and rotational mechanism, and the second adapter is configured so as to operably couple the medical instrument to the distal support.

15. The medical instrument driver of claim 9, further comprising at least one sensor configured and arranged for measuring a force between the distal support and the patient and a force of needle insertion into the tissue.

16. The medical instrument driver of claim 9, wherein the upper mechanism and the lower mechanism are arranged such that at least a portion of the upper mechanism and at least a portion of the lower mechanism are positioned along the long axis of the medical instrument.

17. A medical instrument driver for causing a medical instrument to be inserted into tissue of a patient, comprising:
   an upper mechanism having a translation and rotational mechanism operably coupled to a proximal portion of the medical instrument, the translation and rotational mechanism including:
      a translation structure being configured to translate the medical instrument along a long axis of the medical instrument responsive to rotational movement of an end of such structure, and
      a rotational structure configured to rotate the medical instrument about the long axis as the medical instrument translates along the long axis; and
   a lower mechanism having a distal support that is distal from the translation and rotational mechanism, the distal support having an aperture in which a distal portion of the medical instrument is slidably disposed, wherein
   the distal support and the translation and rotational mechanism are arranged such that the distal portion of the medical instrument moves through the aperture, and an insertable end of the medical instrument exits the aperture and is capable of being inserted into the tissue of the patient,
   during insertion of the medical instrument into the tissue, the upper mechanism moves along the long axis while the lower mechanism remains substantially fixed, thereby limiting movement of the medical instrument in a plane perpendicular to the long axis during the insertion, and
   the medical instrument driver further comprises a first adapter and a second adapter, wherein the first adapter is configured to operably couple the medical instrument to the translation and rotational mechanism, and the second adapter is configured so as to operably couple the medical instrument to the distal support.

18. An apparatus for causing a medical instrument to be inserted into tissue, said apparatus comprising:
   a robotic device having an arm that is movable in one or more dimensions;
   a medical instrument driver operably coupled to the medical instrument and operably coupled to the robotic arm, wherein the robotic arm is movable so as to position the medical instrument driver with respect to a target area, wherein said medical instrument driver includes:
      an upper mechanism having a translation and rotational mechanism operably coupled to a proximal portion of the medical instrument via a proximal portion of the robotic arm, the translation and rotational mechanism including:
         a translation structure being configured to move the medical instrument along a long axis of the medical instrument responsive to rotational movement of an end of such structure, and
         a rotational structure configured to rotate the medical instrument about the long axis as the medical instrument moves along the long axis; and
      a lower mechanism having a distal support operably coupled to a distal portion of the robotic arm and which is distal from the translation and rotational mechanism, said distal support including an aperture in which a distal portion of the medical instrument is slidably disposed, wherein
   the distal support and the translation and rotational mechanism are arranged so the distal portion of the medical instrument moves through and exits the distal support through the aperture such that an insertable end of the medical instrument is capable of being inserted into the tissue of the patient,
   during insertion of the medical instrument into the tissue, the upper mechanism moves along the long axis while the lower mechanism remains substantially fixed, thereby limiting movement of the medical instrument in a plane perpendicular to the long axis during the insertion, and
   the apparatus further comprises a first adapter and a second adapter, wherein the first adapter is configured to operably couple the medical instrument to the translation and rotational mechanism, and the second adapter is configured so as to operably couple the medical instrument to the distal support.

* * * * *